(12) United States Patent
Yukita et al.

(10) Patent No.: US 11,331,211 B2
(45) Date of Patent: May 17, 2022

(54) MOUTHPIECE, SHEET FOR PRODUCTION OF MOUTHPIECE PIECE UNIT, AND PRODUCTION METHOD OF MOUTHPIECE

(71) Applicant: Mitsui Chemicals, Inc., Tokyo (JP)

(72) Inventors: Takashi Yukita, Chiba (JP); Maki Yamamoto, Sodegaura (JP); Hideyuki Nagai, Iwakuni (JP); Yasufumi Tsuchiya, Funabashi (JP)

(73) Assignee: MITSUI CHEMICALS, INC., Tokyo (JP)

( * ) Notice: Subject to any disclaimer, the term of this patent is extended or adjusted under 35 U.S.C. 154(b) by 751 days.

(21) Appl. No.: 16/076,129

(22) PCT Filed: Feb. 27, 2017

(86) PCT No.: PCT/JP2017/007518
§ 371 (c)(1),
(2) Date: Aug. 7, 2018

(87) PCT Pub. No.: WO2017/154641
PCT Pub. Date: Sep. 14, 2017

(65) Prior Publication Data
US 2020/0390594 A1    Dec. 17, 2020

(30) Foreign Application Priority Data

Mar. 8, 2016 (JP) .............................. JP2016-044866
Apr. 15, 2016 (JP) .............................. JP2016-081807
(Continued)

(51) Int. Cl.
*A61F 5/56* (2006.01)
*C08L 23/08* (2006.01)
*C08L 23/12* (2006.01)

(52) U.S. Cl.
CPC .......... *A61F 5/566* (2013.01); *C08L 23/0815* (2013.01); *C08L 23/12* (2013.01); *A61F 2005/563* (2013.01)

(58) Field of Classification Search
CPC ...... C08L 23/0815; C08L 23/12; A61F 5/566; A61F 2005/563
(Continued)

(56) References Cited

U.S. PATENT DOCUMENTS 6,626,180 B1    9/2003 Kittelsen et al.
2002/0051951 A1    5/2002 Chishti et al.
(Continued)

FOREIGN PATENT DOCUMENTS

CN    103588917 A    2/2014
JP    61100273 A    5/1986
(Continued)

OTHER PUBLICATIONS

JP 2012-040136 A, machine translation, EPO Espacenet. (Year: 2012).*
(Continued)

*Primary Examiner* — Josephine L Chang
(74) *Attorney, Agent, or Firm* — Buchanan Ingersoll & Rooney PC

(57) ABSTRACT

A mouthpiece including a constituent portion (X) that includes an olefin-based polymer (A) having a repeating unit having 2 or 3 carbon atoms and that satisfies a bending elastic modulus ($\alpha$) at 23° C. of 80 MPa$\leq\alpha\leq$1000 MPa.

7 Claims, 13 Drawing Sheets

(30) Foreign Application Priority Data

May 25, 2016 (JP) .............................. JP2016-104694
Jul. 1, 2016 (JP) .............................. JP2016-131886

(58) Field of Classification Search
USPC ....................................................... 433/214
See application file for complete search history.

(56) References Cited

U.S. PATENT DOCUMENTS

| | | |
|---|---|---|
| 2003/0190575 A1 | 10/2003 | Hilliard |
| 2005/0256276 A1* | 11/2005 | Elkin ................... A61C 9/0006 525/400 |
| 2006/0019213 A1 | 1/2006 | Graham et al. |
| 2007/0224567 A1 | 9/2007 | Robson |
| 2007/0254256 A1 | 11/2007 | Farrell |
| 2008/0138766 A1 | 6/2008 | Jansheski |
| 2010/0196837 A1 | 8/2010 | Farrell |
| 2011/0020761 A1 | 1/2011 | Kalili |
| 2011/0091833 A1 | 4/2011 | Farrell |
| 2012/0196243 A1 | 8/2012 | Farrell |
| 2012/0220728 A1 | 8/2012 | Uekusa et al. |
| 2012/0295211 A1 | 11/2012 | Frantz et al. |
| 2013/0074851 A1 | 3/2013 | Herman et al. |
| 2013/0244195 A1 | 9/2013 | Farrell |
| 2013/0302742 A1 | 11/2013 | Li et al. |
| 2015/0007830 A1* | 1/2015 | Remmers ............... A61C 19/06 128/848 |
| 2015/0059766 A1 | 3/2015 | Frantz et al. |
| 2015/0182374 A1 | 7/2015 | Stenberg et al. |
| 2015/0216716 A1 | 8/2015 | Anitua Aldecoa |
| 2015/0250642 A1 | 9/2015 | Miquel |
| 2016/0106572 A1 | 4/2016 | Frantz et al. |

FOREIGN PATENT DOCUMENTS

| | | | |
|---|---|---|---|
| JP | 63099857 A | | 5/1988 |
| JP | H04-28381 A | | 1/1992 |
| JP | 0739554 A | | 2/1995 |
| JP | 2002355352 A | | 12/2002 |
| JP | 2008531234 A | | 8/2008 |
| JP | 2008264583 A | | 11/2008 |
| JP | 2010501261 A | | 1/2010 |
| JP | 2012040136 A | * | 3/2012 |
| JP | 2012223587 A | | 11/2012 |
| JP | 2013-533756 A | | 8/2013 |
| JP | 5815668 B2 | | 11/2015 |
| JP | 2016140702 A | * | 8/2016 |
| WO | 2008023799 A1 | | 2/2008 |
| WO | 2009029886 A1 | | 3/2009 |
| WO | 2015/049321 A2 | | 4/2015 |
| WO | 2015053808 A1 | | 4/2015 |

OTHER PUBLICATIONS

JP 2016-140702 A, machine translation, EPO Espacenet. (Year: 2016).*
International Search Report (PCT/ISA/210) dated May 23, 2017, by the Japanese Patent Office as the International Searching Authority for International Application No. PCT/JP2017/007518.
Written Opinion (PCT/ISA/237) dated May 23, 2017, by the Japanese Patent Office as the International Searching Authority for International Application No. PCT/JP2017/007518.
Notice of Reasons for Rejection issued by the Japanese Patent Office in corresponding Japanese Patent Application No. 2018-504380 dated Jul. 2, 2019 (7 pages including partial English translation).
Office Action (Notice of Reasons for Rejection) dated May 19, 2020, by the Japanese Patent Office in corresponding Japanese Patent Application No. 2019-196252 and an English Translation of the Office Action. (5 pages).
Communication pursuant to Rule 164(1) EPC issued by the European Patent Office in corresponding European Application No. 17762981.3-1126 dated Oct. 14, 2019 (12 pages).
Extended European Search Report dated Dec. 15, 2020, issued by the European Patent Office in corresponding European Application No. 20206930.8-1126, (6 pages).

* cited by examiner

MOUTHPIECE, SHEET FOR PRODUCTION OF MOUTHPIECE PIECE UNIT, AND PRODUCTION METHOD OF MOUTHPIECE

TECHNICAL FIELD

The present invention relates to a mouthpiece, a sheet for production of a mouthpiece piece unit, and a production method of a mouthpiece.

BACKGROUND ART

Obstructive sleep apnea syndrome is said to be mainly caused by occluding the airway due to dropping of the mandible, and various mouthpieces and the like have been proposed in order to improve obstructive sleep apnea syndrome. Mouthpieces and the like improve apnea and snoring during sleep by putting the mandible forward over the maxillary and thus keeping the airway wide in wearing.

For example, an oral device is disclosed which includes an upper tray and a lower tray which are to be fitted in the upper and lower rows of teeth of a patient, respectively, a first retention hook set surrounded by the upper tray, an occlusal pad set into which a second retention hook set surrounded by the lower tray is incorporated, and an attachment/detachment unit of the front part and the rear part of each of the upper and lower trays by disposing of a pair of elastic bands onto the first retention hook and the second retention hook in order to enable the mandible of the patient to move forward in fitting of the upper and lower trays to the respective rows of teeth of the patient (see, for example, Japanese Patent Publication (JP-B) No. 5815668). In the oral device, the distance between the retention hooks can be regulated by exchange of the elastic bands.

For example, a dental orthotic is disclosed which includes a maxillary orthotic to be fitted in the row of teeth of the maxillary, a mandible orthotic to be fitted in the row of teeth of the mandible, and an occlusal system for connection of the maxillary orthotic to the mandible orthotic, in which the occlusal system includes securing portions disposed between the maxillary orthotic and the mandible orthotic, and an arm portion for jointing the securing portions, and the arm portion includes a mechanism that can regulate the distance between the securing portions (see, for example, U.S. Patent publication (US) No. 2007/0224567).

Examples of mouthpieces (also referred to as "mouth guards") for use in dental applications include sporting mouth guards, mouthpieces for orthodontics, mouthpieces for temporomandibular arthrosis, night guards for bruxism, to be worn during sleep, and mouthpieces for obstructive sleep apnea syndrome.

Sporting mouth guards are for the purpose of protecting the gnathic bone, the teeth, the mouth and the like from an external force in contact sports such as boxing and rugby football, and a mouth guard with an ethylene-vinyl acetate copolymer (EVA) (see, for example, JP-B No. 1855802), a mouth guard with EVA and a polyolefin-based resin layered (see, for example, Japanese Patent Application Laid-Open (JP-A) No. 2002-355352), and a mouth guard with silicone rubber (see, for example, JP-B No. 1563289) are disclosed.

Orthodontic mouthpieces are for applying required orthodontic forces to required sites by use of elasticity of materials to thereby move the teeth, and are often demanded to have transparency and sensuousness because of being worn during the day.

JP-A No. 2008-264583 discloses a laminated product based on polycarbonate, a laminated product based on an acrylic resin, and the like. Japanese National-Phase Publication (JP-A) No. 2008-531234 describes acrylic, polycarbonate, urethane, and epoxy materials, and the like, and furthermore JP-A No. H07-39554 describes polymethyl methacrylate and polyolefin-based soft elastic materials, and the like, as polymer materials for mouthpiece formation.

Mouthpieces for obstructive sleep apnea syndrome are for improving upper airway occlusion and snoring by positioning of the mandible and the tongue forward during sleep and widening of the upper airway, and polycarbonate and acrylic resins being hard resins (see, for example, International Publication (WO) No. 2008/023799) are used.

For example, JP-A No. 2002-355352 discloses a mouthpiece having a layered structure of a layer made of a thermoplastic elastomer and a layer made of a polyolefin-based resin having no conglutination property.

JP-A No. 2010-501261 discloses a dental device including at least two thermoformable material layers (paragraph 0016 in the Document).

SUMMARY OF INVENTION

Technical Problem

The oral device and the dental orthotic described in JP-B No. 5815668 and US 2007/0224567 are as follows: the retention pad and the securing portion are embedded, and the upper tray and the lower tray, and the maxillary orthotic and the mandible orthotic are in close contact with the retention pad and the securing portion, respectively. Therefore, a problem is that followability is low and oral comfort is not favorable when any force by bruxism and the like, in particular, any force in the lateral direction (direction in parallel with the row face of teeth) to the attachment member and the like (retention pad, securing portion and the like) is applied.

For example, the silicone rubber and the vinyl-based resin described in JP-B No. 1855802, JP-A No. 2002-355352 and JP-B No. 1563289 have the problems of being easily degenerated, discolored and degraded in the oral cavity and of causing bacteria to be easily grown due to porosity thereof. Mouthpieces, however, are generally put in the oral cavity with being worn on the row of teeth of the maxillary or the mandible, and therefore it is also important for mouthpieces to have wear feeling (fitting comfort).

Mouthpieces are also needed to be polished and worked so as to be adapted to the state of the oral cavity, for example, the row of teeth of a wearer or the like in mouthpiece production or according to the growth and/or the variation in row of teeth of a wearer with the lapse of time, and it is also important for mouthpieces to have polishing workability.

The mouth guard (mouthpiece) described in JP-A No. 2002-355352 and the dental device (mouthpiece) described in JP-A No. 2010-501261 may be inferior in wear feeling or durability.

Mouthpieces are also needed to be polished and worked so as to be adapted to the state of the oral cavity, for example, the row of teeth of a wearer or the like in mouthpiece production or according to the growth and/or the variation in the row of teeth of a wearer with the lapse of time, and it is also important for mouthpieces to have polishing workability. The mouthpiece formed by use of an ethylene-vinyl acetate copolymer, polymethyl methacrylate or the like, however, has the problem of being low in polishing workability.

A sheet for production of a mouthpiece piece unit, for use in mouthpiece production, is desirably excellent in moldability and easy in mouthpiece production.

Accordingly, an object of a first aspect of the invention is to provide a mouthpiece excellent in followability and high in oral comfort in application of any force in the lateral direction (direction in parallel with the row face of teeth) to an attachment member by bruxism and the like.

An object of a second aspect of the invention is to provide a mouthpiece excellent in both of wearing property and polishing workability, a sheet for production of a mouthpiece piece unit, and a production method of a mouthpiece.

An object of a third aspect of the invention is to provide a mouthpiece easy in production and excellent in wear feeling and durability, and a production method of a mouthpiece.

An object of a fourth aspect of the invention is to provide a mouthpiece excellent in polishing workability, a sheet for production of a mouthpiece piece unit, which is excellent in moldability and enables a mouthpiece excellent in polishing workability to be produced, and a production method of a mouthpiece excellent in polishing workability.

Solution to Problem

Examples of the first aspect of the invention include the following implementation aspects <1> to <11>.

Examples of the second aspect of the invention include the following implementation aspects <12> to <23>.

Examples of the third aspect of the invention include the following implementation aspects <24> to <32>.

Examples of the fourth aspect of the invention include the following implementation aspects <33> to <42>.

<1> A mouthpiece including: a first piece that is to be worn on at least right and left back portions of rows of teeth and that has first through-holes, penetrating through right and left outer wall portions in a thickness direction, located outside the rows of teeth in each of the right and left outer wall portions; a second piece that is to be worn on at least right and left back portions of rows of teeth and that has second through-holes, penetrating through right and left outer wall portions in a thickness direction, located outside the rows of teeth in each of the right and left outer wall portions; first attachment members each including a first base portion that is inserted into one of the first through-holes and that does not protrude, but is exposed from a wall surface of one of the outer wall portions, the wall surface being closer to the row of teeth, and first attachment portions that protrude from the wall surfaces of the outer wall portions, the wall surfaces being located opposite to the row of teeth; second attachment members each including a second base portion that is inserted into one of the second through-holes and that does not protrude, but is exposed from a wall surface of one of the outer wall portions, the wall surface being closer to the row of teeth, and second attachment portions that protrude from the wall surfaces of the outer wall portions, the wall surfaces being located opposite to the row of teeth; and a pair of joining members each including a first joint portion and a second joint portion attached to the first attachment portion at right and left locations and the second attachment portion at right and left locations, respectively, and that openably and closably join the first piece and the second piece.

<2> The mouthpiece according to <1>, wherein at least one of the first attachment member or the second attachment member is removable from the piece.

<3> The mouthpiece according to <1> or <2>, wherein the mouthpiece includes a structure in which each outer wall portion of the first piece is sandwiched between the first base portion of the first attachment member and the first joint portion of the joining member attached to the first attachment portion of the first attachment member, and each outer wall portion of the second piece is sandwiched between the second base portion of the second attachment member and the second joint portion of the joining member attached to the second attachment portion of the second attachment member, or a structure in which a first sandwiching member is disposed on each first attachment portion to sandwich the outer wall portion of the first piece between the first sandwiching member and the first base portion of the first attachment member, and a second sandwiching member is disposed on each second attachment portion to sandwich the outer wall portion of the second piece between the second sandwiching member and the second base portion of the second attachment member.

<4> The mouthpiece according to <3>, wherein a portion of the first piece, sandwiched between the first base portion and the first joint portion or the first sandwiching member, and a portion of the second piece, sandwiched between the second base portion and the second joint portion or the second sandwiching member, are formed from a material having a tensile strength of 150 N or more and less than 2000 N.

<5> The mouthpiece according to <4>, wherein the material is an olefin-based resin.

<6> The mouthpiece according to any one of from <1> to <5>, wherein the first base portion of each first attachment member is accommodated in one of the first through-holes so as to serve as a depressed portion with respect to a wall surface of one of the outer walls portion, the wall surface being closer to the row of teeth, and the second base portion of each second attachment member is accommodated in one of the second through-holes so as to serve as a depressed portion with respect to a wall surface of one of the outer wall portions, the wall surface being closer to the row of teeth.

<7> The mouthpiece according to any one of from <1> to <6>, wherein the joining member has a non-step regulation function that regulates the distance between the first attachment member and the second attachment member.

<8> The mouthpiece according to any one of from <1> to <7>, wherein the joining member is formed from plastic.

<9> The mouthpiece according to any one of from <1> to <8>, wherein the first piece is a maxillary piece to be worn on the row of teeth on at least right and left back portions of the maxillary and the second piece is a mandible piece to be worn on the row of teeth on at least right and left back portions of the mandible, and a section where each first attachment member is inserted into and attached to one of the first through-holes lies rearward of a section where a corresponding second attachment member is inserted into and attached to one of the second through-holes, as viewed from a center of the row of teeth.

<10> The mouthpiece according to <9>, wherein the maxillary piece is worn on the row of teeth on the right and left back of the maxillary.

<11> The mouthpiece according to any one of from <1> to <10>, wherein a cross section of the first base portion, perpendicularly intersecting with a thickness direction of the first piece, and a cross section of the second base portion, perpendicularly intersecting with a thickness direction of the second piece, are at least one of bilaterally symmetric or vertically symmetric.

<12> A mouthpiece including a constituent portion (X), the constituent portion (X) including an olefin-based polymer (A) having a repeating unit having 2 or 3 carbon atoms and satisfying a bending elastic modulus (a) at 23° C. of 80 MPa≤α≤1000 MPa.

<13> The mouthpiece according to <12>, wherein the olefin-based polymer (A) has a structural unit derived from a siloxane structure.

<14> The mouthpiece according to <12> or <13>, wherein the constituent portion (X) has a layered structure including a layer (LI) that satisfies a bending elastic modulus (α1) at 23° C. of 5 MPa≤α1≤100 MPa, and a layer (LO) that satisfies a bending elastic modulus (α2) at 23° C. of 200 MPa≤α2≤1500 MPa.

<15> The mouthpiece according to <14>, wherein the layer (LI) is exposed at at least a part of an outermost surface of the constituent portion (X).

<16> The mouthpiece according to <15>, wherein the constituent portion (X) is a portion to be brought into contact with the teeth in wearing of the mouthpiece on a row of teeth, and the layer (LI) is exposed at at least a part of a surface of the portion to be brought into contact with the teeth.

<17> The mouthpiece according to any one of from <12> to <16>, wherein the water absorption rate (β) in immersion of the constituent portion (X) dried at 50° C. for 24 hours in a water bath at 37° C. for 24 hours satisfies 0%≤β≤1.0%.

<18> The mouthpiece according to any one of from <12> to <17>, wherein the constituent portion (X) is a piece unit to be worn on a row of teeth.

<19> The mouthpiece according to any one of from <12> to <18>, wherein the constituent portion (X) has a thickness of from 0.3 to 5.0 mm.

<20> The mouthpiece according to any one of from <12> to <19>, wherein the mouthpiece is a mouthpiece for temporomandibular joint syndrome or a mouthpiece for sleep apnea syndrome.

<21> The mouthpiece according to any one of from <12> to <20>, wherein the mouthpiece is a mouthpiece including a maxillary piece, a mandible piece, and a joining member that joints the maxillary piece and the mandible piece, and at least one of the maxillary piece or the mandible piece includes the constituent portion (X).

<22> A sheet for production of a mouthpiece piece unit, the sheet including an olefin-based polymer (A) having a repeating unit having 2 or 3 carbon atoms, and satisfying a bending elastic modulus (a) at 23° C. of 80 MPa≤α≤1000 MPa.

<23> A production method of a mouthpiece, the method including a step of hot forming a sheet for production of a mouthpiece piece unit, the sheet including an olefin-based polymer (A) having a repeating unit having 2 or 3 carbon atoms, and satisfying a bending elastic modulus (a) at 23° C. of 80 MPa≤α≤1000 MPa to provide a mouthpiece piece unit.

<24> A mouthpiece to be worn on a row of teeth, wherein the mouthpiece has a layered structure including a layer (A) closer to the row of teeth when the mouthpiece is worn on the row of teeth, and a layer (B) layered on the layer (A) and disposed opposite to the row of teeth when the mouthpiece is worn, as viewed from the layer (A), the layer (A) contains at least one elastomer selected from the group consisting of an acrylic thermoplastic elastomer and a polyester-based thermoplastic elastomer, the layer (B) contains at least one polymer selected from the group consisting of poly(meth)acrylate and polyester, an adhesion strength between the layer (A) and the layer (B) is 30 MPa or more, a bending elastic modulus of the layer (A) is from 50 MPa to 300 MPa, a bending elastic modulus of the layer (B) is higher than the bending elastic modulus of the layer (A), and a difference between the bending elastic modulus of the layer (A) and the bending elastic modulus of the layer (B) is from 1000 MPa to 3000 MPa.

<25> The mouthpiece according to <24>, wherein the acrylic thermoplastic elastomer is a block copolymer including a hard block and a soft block, and a glass transition temperature of the hard block of the acrylic thermoplastic elastomer is higher than a glass transition temperature of the soft block of the acrylic thermoplastic elastomer.

<26> The mouthpiece according to <25>, wherein both the hard block and the soft block of the acrylic thermoplastic elastomer have an alkyl (meth)acrylate unit derived from alkyl (meth)acrylate, and the number of carbon atoms of an alkyl portion of the alkyl (meth)acrylate unit in the soft block is larger than the number of carbon atoms of an alkyl portion of the alkyl (meth)acrylate unit in the hard block.

<27> The mouthpiece according to any one of from <24> to <26>, wherein the polyester-based thermoplastic elastomer is a block copolymer including a hard block and a soft block, and a glass transition temperature of the hard block of the polyester-based thermoplastic elastomer is higher than a glass transition temperature of the soft block of the polyester-based thermoplastic elastomer.

<28> The mouthpiece according to <27>, wherein the hard block of the polyester-based thermoplastic elastomer includes a structural unit having an ester structure, and the soft block of the polyester-based thermoplastic elastomer includes a structural unit having an ester polyol structure.

<29> The mouthpiece according to any one of from <24> to <28>, wherein the mouthpiece is a mouthpiece for temporomandibular joint syndrome or a mouthpiece for sleep apnea syndrome.

<30> A production method of a mouthpiece to be worn on a row of teeth, in which the mouthpiece has a layered structure including a layer (A) closer to the row of teeth when the mouthpiece is worn on the row of teeth and a layer (B) layered on the layer (A) and disposed opposite to the row of teeth when the mouthpiece is worn, as viewed from the layer (A), the layer (A) contains at least one elastomer selected from the group consisting of an acrylic thermoplastic elastomer and a polyester-based thermoplastic elastomer, and the layer (B) contains poly(meth)acrylate, the method including a step of hot forming an elastomer sheet containing the at least one elastomer to thereby form the layer (A), and a step of building up a precursor of poly(meth)acrylate on the layer (A) and then curing the resultant to thereby form the layer (B) containing poly(meth)acrylate.

<31> A production method of a mouthpiece to be worn on a row of teeth, in which the mouthpiece has a layered structure including a layer (A) closer to the row of teeth when the mouthpiece is worn on the row of teeth and a layer (B) layered on the layer (A) and disposed opposite to the row of teeth when the mouthpiece is worn, as viewed from the layer (A), the layer (A) contains at least one elastomer selected from the group consisting of an acrylic thermoplastic elastomer and a polyester-based thermoplastic elastomer, and the layer (B) contains polyester, the method including a step of hot forming a layered sheet including an elastomer sheet containing the at least one elastomer and a polyester sheet layered on the elastomer sheet, containing polyester, to thereby provide a mouthpiece having the layered structure.

<32> A production method of a mouthpiece to be worn on a row of teeth, in which the mouthpiece has a layered structure including a layer (A) closer to the row of teeth the mouthpiece is worn on the row of teeth and a layer (B)

layered on the layer (A) and disposed opposite to the row of teeth when the mouthpiece is worn, as viewed from the layer (A), the layer (A) contains at least one elastomer selected from the group consisting of an acrylic thermoplastic elastomer and a polyester-based thermoplastic elastomer, and the layer (B) contains at least one polymer selected from the group consisting of poly(meth)acrylate and polyester, the method including a step of hot forming an elastomer sheet containing the at least one elastomer to thereby form the layer (A), and a step of heat-sealing a sheet containing the at least one polymer onto the layer (A), to thereby form the layer (B) containing the at least one polymer.

<33> A mouthpiece including a constituent portion (X), the constituent portion including an olefin-based polymer (A) having a repeating unit having 2 or 3 carbon atoms and satisfying a Shore A hardness of more than 80 and less than 86.

<34> The mouthpiece according to <33>, wherein the olefin-based polymer (A) has a structural unit derived from a siloxane structure.

<35> The mouthpiece according to <33> or <34>, wherein the mouthpiece satisfies the following conditions (a) to (c):
(a) the olefin-based polymer (A) includes, with respect to 100 parts by mass of the olefin-based polymer (A), from 51 parts by mass to 90 parts by mass of an olefin-based polymer component (A-1) having a melting point of from 100° C. to 170° C. measured according to a DSC method; (b) the olefin-based polymer (A) includes, with respect to 100 parts by mass of the olefin-based polymer (A), from 10 parts by mass to 49 parts by mass of an olefin-based polymer component (A-2) having a melting point of 95° C. or less or having substantially absent melting point, measured according to a DSC method; and (c) the olefin-based polymer (A) has a bending elastic modulus (a) at 23° C., of 5 MPa≤α≤100 MPa.

<36> The mouthpiece according to any one of from <33> to <35>, wherein the constituent portion (X) has a thickness of from 0.3 mm to 5.0 mm.

<37> The mouthpiece according to any one of from <33> to <36>, wherein the constituent portion (X) has an impact resilience rate (γ) of 0%≤γ≤25%.

<38> The mouthpiece according to any one of from <33> to <37>, wherein the water absorption rate (β) in immersion of the constituent portion (X) dried at 50° C. for 24 hours in a water bath at 37° C. for 24 hours satisfies 0≤β≤1.0%.

<39> The mouthpiece according to any one of from <33> to <38>, wherein the constituent portion (X) is a piece unit to be worn on a row of teeth.

<40> The mouthpiece according to any one of from <33> to <39>, wherein the mouthpiece is a mouthpiece for temporomandibular joint syndrome or a mouthpiece for sleep apnea syndrome.

<41> A sheet for production of a mouthpiece piece unit, the sheet including an olefin-based polymer (A) having a repeating unit having 2 or 3 carbon atoms, and satisfying a Shore A hardness of more than 80 and less than 86.

<42> A production method of a mouthpiece, the method including a step of hot forming a sheet for production of a mouthpiece piece unit, the sheet including an olefin-based polymer (A) having a repeating unit having 2 or 3 carbon atoms, and satisfying a Shore A hardness of more than 80 and less than 86, to provide a mouthpiece piece unit.

Advantageous Effects of Invention

According to the first aspect, there can be provided a mouthpiece excellent in followability and high in oral comfort in application of any force in the lateral direction (direction in parallel with the row face of teeth) to an attachment member by bruxism and the like.

According to the second aspect, there can be provided a mouthpiece excellent in both of wearing property and polishing workability, a sheet for production of a mouthpiece piece unit, and a production method of a mouthpiece.

According to the third aspect, there can be provided a mouthpiece easy in production and excellent in wear feeling and durability, and a production method thereof.

According to the fourth aspect, there can be provided a mouthpiece excellent in polishing workability, a sheet for production of a mouthpiece piece unit, which is excellent in moldability and enables a mouthpiece excellent in polishing workability to be produced, and a production method of a mouthpiece excellent in polishing workability.

DESCRIPTION OF EMBODIMENTS

Figure 1:
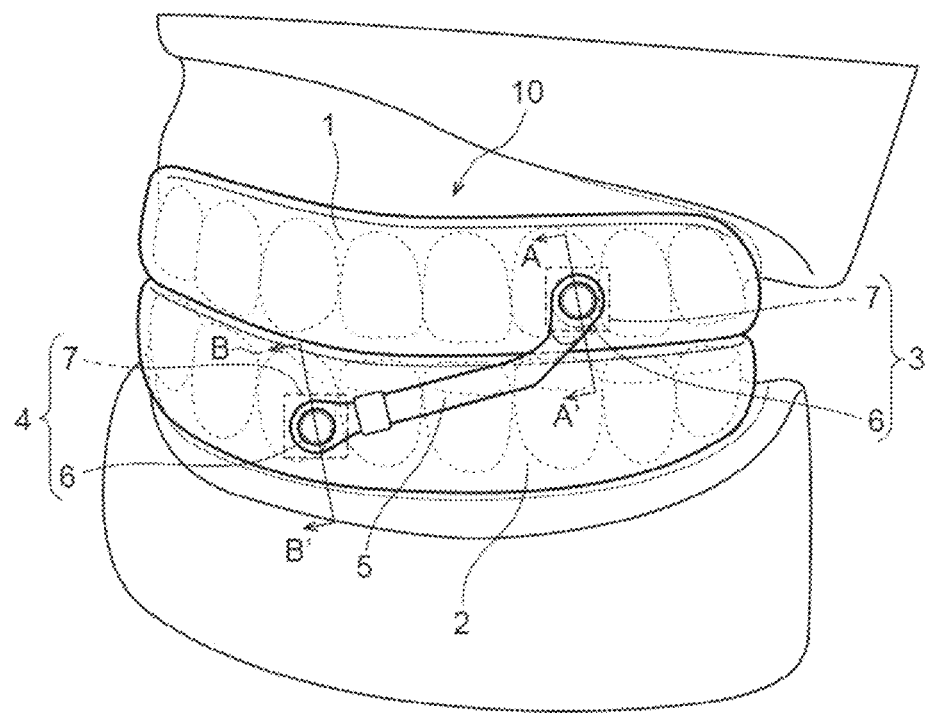
FIG. 1 includes aside view illustrating a schematic configuration of a mouthpiece according to one example of the first aspect.

The numerical value range represented by using the term "to" herein indicates a range including the numerical values described before and after the term "to" as the lower limit and the upper limit, respectively.

The amount of each component in a composition herein means, if multiple relevant substances are present in such each component in a composition, the total amount of the substances present in a composition, unless particularly noted.

The term "(meth)acrylic" herein is used in concept of encompassing both of acrylic and methacrylic, and the term "(meth)acrylate" herein is used in concept of encompassing both of acrylate and methacrylate.

The term "step" herein includes not only an independent step, but also a step as long as any given object of the step is achieved, even if such a step cannot be clearly distinguished from other steps.

The concept of the "mouthpiece" herein encompasses not only one commonly referred to as "mouthpiece", but also one referred to as "mouth guard".

The "front" herein refers to an outside (closer to the lip in mouthpiece wearing) when viewed from the front face in a case in which a mouthpiece is worn and a maxillary piece is located vertically upward to a mandible piece, and the "rear" refers to an inside opposite to the "front" (an inside when viewed from the front face in a case in which the mouthpiece is worn and the maxillary piece is located vertically upward to the mandible piece (closer to the palate in mouthpiece wearing)).

The "right and left" herein refers to a direction perpendicular to each of the front and rear direction and the upward and downward direction (vertically upward and vertically downward) when viewed from the front face in a case in which a mouthpiece is worn and a maxillary piece is located vertically upward to a mandible piece. The "right" corresponds to the left"of the mouthpiece and the left" corresponds to the "right" of the mouthpiece, when viewed from the front face.

The "cross section being bilaterally symmetric" herein refers to being symmetric in a direction perpendicular to the upward and downward direction (vertically upward and vertically downward).

Hereinafter, examples of the first aspect to fourth aspect of the invention are described with reference to the drawings, but the invention is not intended to be limited to the aspects illustrated in the drawings. The size of each member in each drawing is conceptual, and a relative relationship of the size between members is not limited thereto. Members having a substantially same function are denoted by the same reference numeral throughout all the drawings, and an overlapped description may be omitted.

<First Aspect>
[Mouthpiece]

A mouthpiece 10 according to the first aspect includes a maxillary piece (first piece) 1 which is to be worn on the row of teeth of the maxillary, a mandible piece (second piece) 2 which is to be worn on the row of teeth of the mandible, a maxillary attachment member (first attachment member, hereinafter, also referred to as "maxillary member") 3 which is inserted into a first through-hole (first through-hole) at each of the right and left locations of the maxillary piece 1 and which has a first attachment portion 3a exposed, a mandible attachment member (second attachment member, hereinafter, also referred to as "mandible member") 4 which is inserted into a through-hole (second through-hole) at each of the right and left locations of the mandible piece 2 and which has a second attachment portion 4a exposed, and a pair of joining members 5 which include a first joint portion and a second joint portion attached to the first attachment portion 3a and second attachment portion 4a at each of the right and left locations, respectively, and which openably and closably joint the maxillary piece 1 and the mandible piece 2.

The mouthpiece 10 is disposed so that the maxillary member 3 and the mandible member 4 are inserted into the through-holes of the maxillary piece 1 and the mandible piece 2 at each of the right and left locations, respectively, and both faces thereof are exposed from the maxillary piece 1 and the mandible piece 2 in the thickness directions of the maxillary piece 1 and the mandible piece 2, respectively. Therefore, the mouthpiece 10 is more excellent in followability in application of any force in the lateral direction (direction in parallel with the row face of teeth) to the maxillary member 3 or the mandible member 4 by the bruxism and the like, and higher in oral comfort than a mouthpiece with an attachment member being embedded in a piece.

The mouthpiece 10 includes the maxillary piece 1 and the mandible piece 2. The maxillary piece 1 is a member to be worn to the row of teeth of the maxillary. The maxillary piece 1 has each through-hole penetrating through an outer wall portion closer to the maxillary (first outer wall portion) positioned outside the row of teeth in the thickness direction, towards the right and left rear (from the sixth to the seventh in the row of teeth in FIG. 1) when viewed from the center of the row of teeth, and the maxillary member 3 is inserted into each through-hole. The mandible piece 2 is a member to be worn to the row of teeth of the mandible, the mandible piece 2 has each through-hole penetrating through an outer wall portion closer to the mandible (second outer wall portion) positioned outside the row of teeth in the thickness direction, towards the right and left front (from the third to the fourth in the row of teeth in FIG. 1) when viewed from the center of the row of teeth, and the mandible member 4 is inserted into each through-hole.

The configuration can be adopted to thereby ensure the mobility of each of the maxillary piece 1 and the mandible piece 2 to some extent particularly in application of any force in the lateral direction (direction in parallel with the row face of teeth) to the maxillary member 3, the mandible member 4 and the like by the bruxism and the like, thereby providing a mouthpiece 10 high in oral comfort. On the other hand, in application of any force to the maxillary piece 1 and the mandible piece 2 (force in a direction in parallel with the longer axis direction of the joining members 5), the configuration can be adopted to thereby suppress the mobility of each of the maxillary piece 1 and the mandible piece 2 and thus sufficiently ensure the position of the maxillary and the mandible.

The maxillary piece may be configured so as to be worn on the row of teeth on at least the right and left back of the maxillary, or the maxillary piece may be configured so as not to be provided on the center portion of the row of teeth of the maxillary. The maxillary piece may also be configured so as not to be provided on the center portion of the row of teeth of the maxillary, but to be mutually jointed by a wire or the like with being worn on the row of teeth on the right and left back of the maxillary. Much the same is true on the mandible piece.

Figure 5:
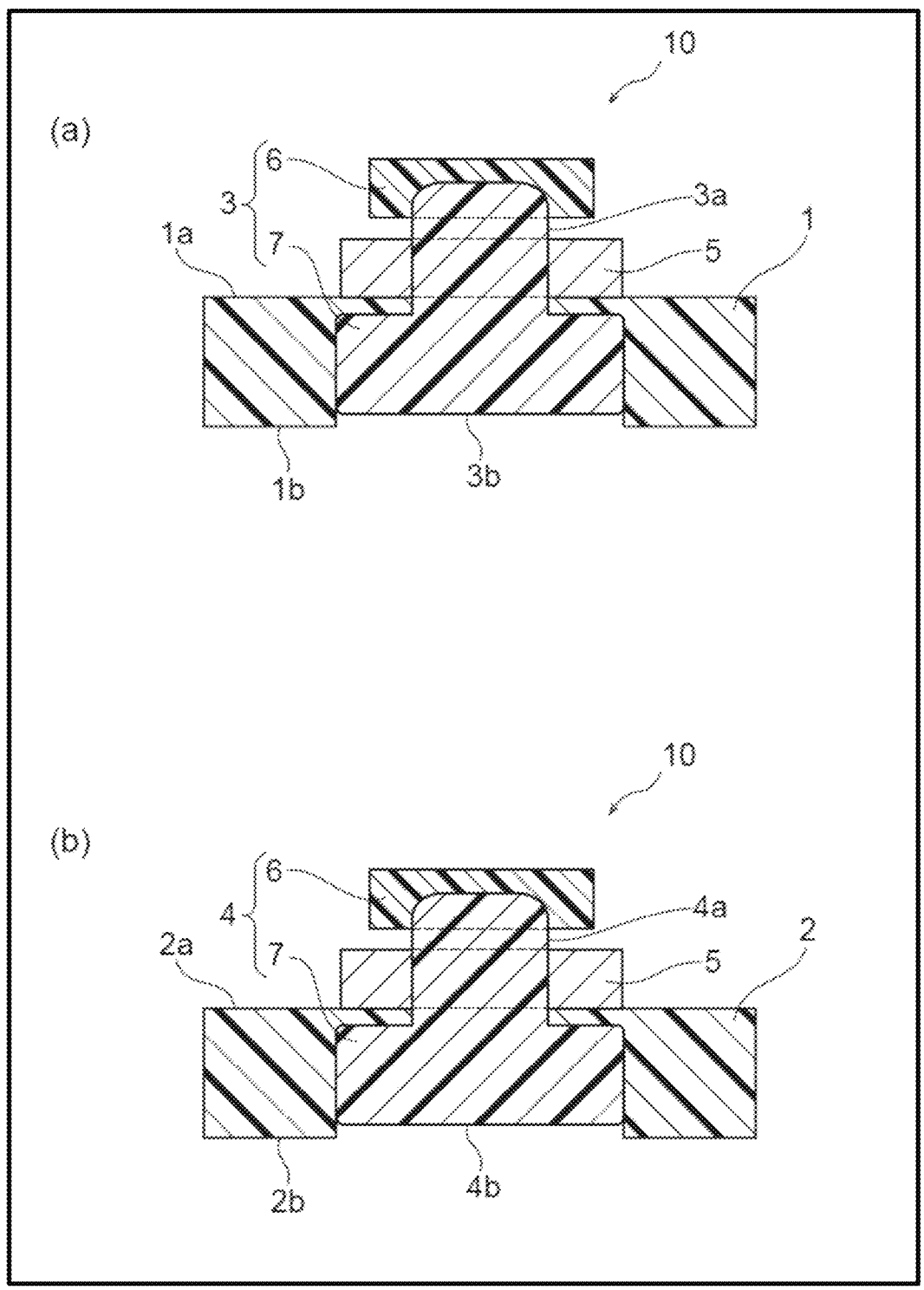
FIG. 5(a) includes an A-A' line cross-sectional view of FIG. 1 and FIG. 5(b) includes a B-B' line cross-sectional view of FIG. 1.

The mouthpiece 10 includes the maxillary member 3 and the mandible member 4. The maxillary member 3 is a member disposed so that the member is inserted into a through-hole at each of the right and left locations, provided on the maxillary piece 1, and both ends thereof are exposed from the maxillary piece 1 in the thickness direction of the maxillary piece 1. The maxillary member 3 further includes a first base portion which does not protrude, but is exposed from a wall surface 1b of the outer wall portion closer to the maxillary, the wall surface 1b closer to the row of teeth, and a first attachment portion 3a which protrudes from a wall surface 1a of the outer wall portion closer to the maxillary, the wall surface 1a being located opposite to the row of teeth. More specifically, the exposed surface (rear surface 3b) of the first base portion of the maxillary member 3 is in plane with the wall surface 1b of the outer wall portion closer to the maxillary the wall surface 1b closer to the row of teeth, or is positioned inward over the wall surface 1b of the outer wall portion closer to the maxillary, the wall surface 1b closer to the row of teeth, as illustrated in FIG. 5(a). The first attachment portion 3a of the maxillary member 3 protrudes from the wall surface 1a of the outer wall portion closer to the maxillary, the wall surface 1a being located opposite to the row of teeth, and is positioned outward over the wall surface 1a.

The mandible member 4 is a member disposed so that the member is inserted into a through-hole at each of the right and left locations, provided on the mandible piece 2, and both ends thereof are exposed from the mandible piece 2 in the thickness direction of the mandible piece 2. The mandible member 4 further includes a second base portion which does not protrude, but is exposed from a wall surface 2b of the outer wall portion closer to the mandible, the wall surface 2b closer to the row of teeth, and a second attachment portion 4a which protrudes from a wall surface 2a of the outer wall portion closer to the mandible, the wall surface 2a being located opposite to the row of teeth. More specifically, the exposed surface (rear surface 4b) of the second base portion of the mandible member 4 is in plane with the wall surface 2b of the outer wall portion closer to the mandible, the wall surface 2b closer to the row of teeth, or is positioned inward over the wall surface 2b of the outer wall portion closer to the mandible, the wall surface 2b closer to the row of teeth, as illustrated in FIG. 5(b). The second attachment portion 4a of the mandible member 4 protrudes from the wall surface 2a of the outer wall portion closer to the mandible, the wall surface 2a being located opposite to the row of teeth, and is positioned outward over the wall surface 2a.

The mouthpiece 10 includes the joining members 5 each having a first joint portion and a second joint portion. The joining members 5 are each a member which is provided rightward and leftward when viewed from the center of the row of teeth, which is attached to the first attachment portion 3a and the second attachment portion 4a located at each of the right and left, through the first joint portion and the second joint portion, respectively, and which openably and closably joints the maxillary member 3 and the mandible member 4. Particularly, the first joint portion and the second joint portion each having a through-hole are fitted in and secured to the first attachment portion 3a and the second attachment portion 4a, respectively.

It is preferable in the mouthpiece 10 that the maxillary member 3 is removable from the maxillary piece 1 and the mandible member 4 is removable from the mandible piece 2. A mouthpiece where an attachment member is embedded into a piece cannot allow the attachment member to be detached from the piece, and the piece is broken if the attachment member is tried to be forcedly detached. On the other hand, the mouthpiece 10 can allow the maxillary member 3 and the mandible member 4 to be detached and exchanged and can be easily cleaned because the maxillary member 3 and the mandible member 4 is removable from the maxillary piece 1 and the mandible piece 2, respectively.

Figure 6:
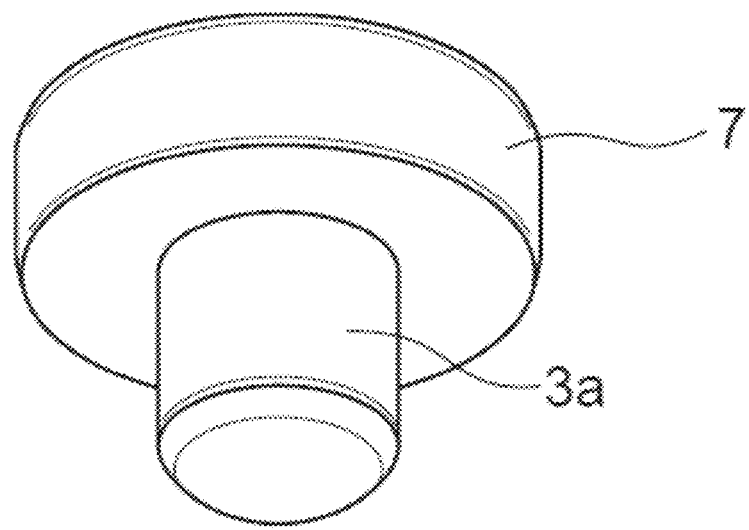
FIG. 6 includes a schematic view representing an opening member and a fitting member forming a maxillary attachment member for use in one example of the first aspect.
Figure 6:
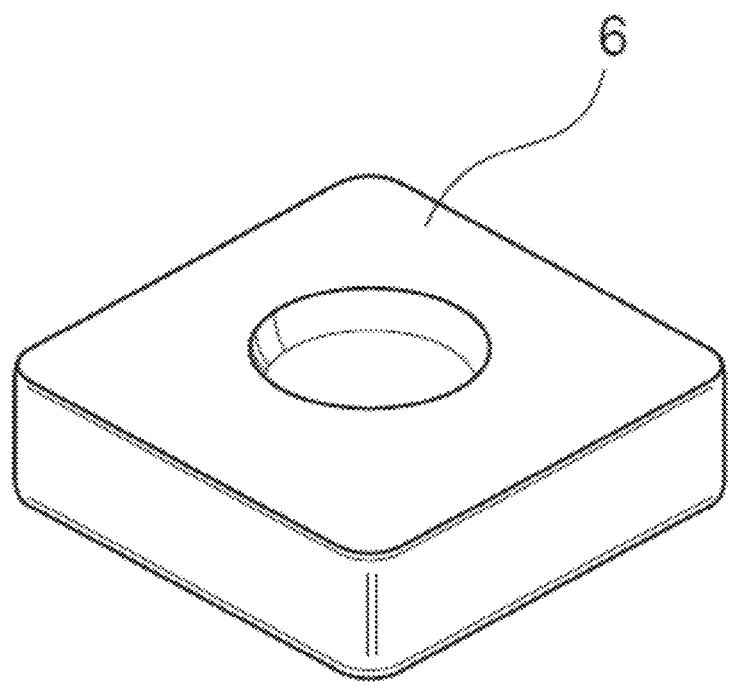

The mouthpiece 10 in which the maxillary member 3 is detachable has a configuration where the maxillary member 3 is formed from an opening member 6 having an opening portion (dotted line region in FIG. 6) and a fitting member 7 having a first attachment portion 3a, fitted into the opening member 6, as illustrated in FIG. 5(a) and FIG. 6. The fitting member 7 is inserted into the through-hole of the maxillary piece 1, and the first attachment portion 3a of the fitting member 7, which protrudes and which is exposed from the maxillary piece 1, is fitted in the opening member 6. The opening portion of the opening member 6 may have a depressed shape, or may be a through-hole. As illustrated in FIG. 5(b), the mandible member 4 is also similarly formed from the opening member 6 and the fitting member 7.

The fitting member 7 includes a first base portion which does not protrude, but is exposed from a wall surface 1b of the outer wall portion closer to the maxillary, the wall surface 1b closer to the row of teeth, and a first attachment portion 3a which protrudes from a wall surface 1a of the outer wall portion closer to the maxillary, the wall surface 1a being located opposite to the row of teeth, in the mouthpiece 10 illustrated in FIG. 5(a).

Other examples of the opening member 6 and the fitting member 7 include an opening member and a rivet, a female screw and a male screw, a snap lock, and a lure lock. The description of a configuration where the mandible member 4 is detachable is omitted because the configuration is similar to the above.

Figure 7:
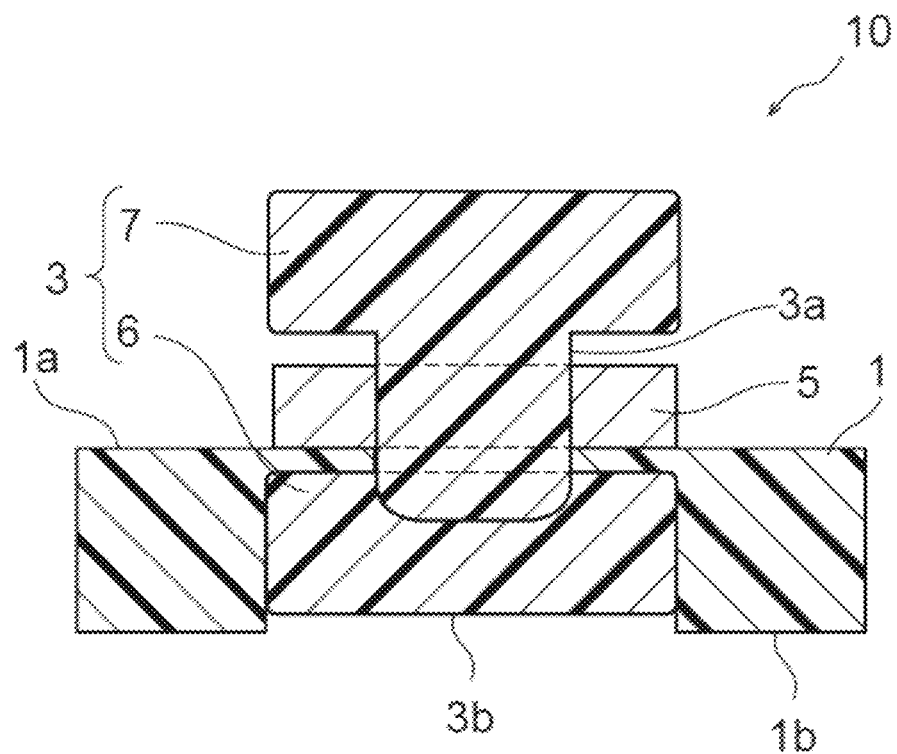
FIG. 7 includes an enlarged view of a mouthpiece according to a modification example of the first aspect.

The mouthpiece 10 may have a positional relationship between the opening member and the fitting member, opposite to the above relationship. That is, an opening member 6 may be attached into a through-hole of a maxillary piece 1 and a fitting member 7 having a first attachment portion 3a may be fitted in the opening member 6, as illustrated in FIG. 7. FIG. 7 is an enlarged view of a mouthpiece according to a modification example.

The opening member 6 forms a first base portion which does not protrude, but is exposed from a wall surface 1b of the outer wall portion closer to the maxillary, the wall surface 1b closer to the row of teeth, and the fitting member 7 forms the first attachment portion 3a which protrudes from a wall surface 1a of the outer wall portion closer to the maxillary, the wall surface 1a being located opposite to the row of teeth, in a mouthpiece 10 illustrated in FIG. 7.

Examples of the maxillary member 3 and the mandible member 4 include those formed from various materials such as a metal and plastic.

It is preferable in the mouthpiece 10 that the maxillary piece 1 is sandwiched between the first base portion of the maxillary member 3 and the first joint portion of the joining member 5 attached to the first attachment portion 3a, and the mandible piece 2 is sandwiched between the second base portion of the mandible member 4 and the second joint portion of the joining member 5 attached to the second attachment portion 4a. Thus, backlash of the maxillary member 3 and the mandible member 4 is suppressed. Therefore, the rear surface 3b of the maxillary member 3 and the rear surface 4b of the mandible member 4 are inhibited from contacting with and applying any force to the gingiva in application of a load to the maxillary member 3 and the mandible member 4, thereby resulting in a reduction in the load to the gingiva.

The mouthpiece according to the present aspect may have a configuration where each of the maxillary piece and the mandible piece is sandwiched using components other than the joining members. For example, the following configuration may be adopted: the maxillary piece is sandwich between a first sandwiching member disposed between the first joint portion and the first base portion, and the first base portion, and the mandible piece is sandwiched between a second sandwiching member disposed between the second joint portion and the second base portion, and the second base portion.

It is preferable in a configuration where the maxillary piece 1 and the mandible piece 2 are sandwiched using the maxillary member 3 and the mandible member 4, respectively, together with the joining member 5 that the distance a between a wall surface 1a of the outer wall portion closer to the maxillary, of the maxillary piece 1, the wall surface 1a being located opposite to the gingiva, and a surface of the first joint portion, the surface facing the maxillary piece 1, is 0 or more and less than 1+b (mm) from the viewpoints of a decrease in any pain to the row face of teeth and retention of the strength to the first joint portion. The reference b represents the thickness of the first joint portion.

It is also preferable that the distance a' between a wall surface 2b of the outer wall portion closer to the mandible, of the mandible piece 2, the wall surface 2b being located opposite to the gingiva, and a surface of the second joint portion, the surface facing the mandible piece 2, is 0 or more and less than 1+b' (mm) from the viewpoints of a decrease in any pain to the row face of teeth and retention of the strength to the second joint portion. The reference b' represents the thickness of the second joint portion.

When the mouthpiece is a push type mouthpiece as described below which pushes the mandible forward in wearing, a force to be applied to the maxillary attachment member and the mandible attachment member is increased to thereby easily cause backlash of the maxillary attachment member and the mandible attachment member, as compared with a pull type mouthpiece which pulls the maxillary forward in wearing. Therefore, the push type mouthpiece is preferably configured so that the maxillary piece and the mandible piece are each sandwiched, from the viewpoint of suitable suppression of backlash of the maxillary attachment member and the mandible attachment member.

It is preferable that surfaces of the first base portion of the maxillary member 3 and the second base portion of the mandible member 4, in contact with the maxillary piece 1 and the mandible piece 2, respectively, have a depression and protrusion shape from the viewpoint of stronger and closer contact of the maxillary piece 1 and the mandible piece 2 with the maxillary member 3 and the mandible member 4.

A portion of the maxillary piece 1, sandwiched between the first base portion and the first joint portion, and a portion of the mandible piece 2, sandwiched between the second base portion and the second joint portion, in the mouthpiece 10 are preferably formed from a material having a tensile strength of 150 N or more and less than 2000 N, more preferably formed from a material having a tensile strength of from 150 N to 1000 N, still more preferably formed from a material having a tensile strength of from 150 N to 500 N. The portions sandwiched are formed from a relatively soft material, thereby allowing the mouthpiece 10 to be high in followability of the maxillary piece 1 and the mandible piece 2 to the teeth in wearing, and to be more excellent in oral comfort.

The tensile strength herein refers to a strength at which breakage occurs when a hole having a diameter of 1.5 mm is created on the sixth of the row of teeth of the maxillary piece of a mouthpiece (thickness: 3 mm) made using a Nissin standard model and a tensile test is conducted in the posterior teeth direction (the rear direction of the row of teeth).

Examples of the material having a tensile strength of 150 N or more and less than 2000 N include an olefin-based resin, a polyester-based resin, a urethane-based resin, a polyamide-based resin and an acrylic rubber resin, and in particular, an olefin-based resin is preferable.

The olefin-based resin is a polymer obtained by homopolymerization of an olefin or a copolymer obtained by polymerization of an olefin with other monomer. Such an olefin is preferably an olefin having from 2 to 6 carbon atoms, and examples thereof include ethylene, propylene, butene, methylpentene and hexene. Examples of such other monomer include vinyl acetate.

The olefin-based resin is preferably polyethylene (PE), a polyethylene-based resin, polypropylene (PP), a polypropylene-based resin or an ethylene-vinyl acetate copolymer (EVA), particularly preferably polyethylene (PE), a polyethylene-based resin, polypropylene (PP) or a polypropylene-based resin.

The polyester-based resin is a polycondensate of polyvalent carboxylic acid (dicarboxylic acid) and polyalcohol (diol), and examples thereof include polyethylene terephthalate (PET).

The urethane-based resin is a polycondensate of a compound having an isocyanate group and a compound having a hydroxyl group, and examples thereof include thermoplastic polyurethane (TPU).

The polyamide-based resin is a polymer made by binding of a large number of monomers by an amide bond, and examples thereof include nylon 6, nylon 11, nylon 12, nylon 66, para amide and meta amide.

The acrylic rubber resin includes acrylic rubber as a main component, and examples thereof include a block copolymer of methyl methacrylate and butyl acrylate.

The material having a tensile strength of 150 N or more and less than 2000 N may be a commercially available product, and NOTIO (registered trademark) produced by Mitsui Chemicals, Inc. may be used as the polypropylene resin.

A common mouthpiece for sleep apnea syndrome is formed from a relatively hard material such as an acrylic resin (for example, having a tensile strength of about 3000 N) as a material forming the maxillary piece and the mandible piece. The reason why the maxillary piece and the mandible piece are each formed from a hard material is because, when the attachment member is embedded in the maxillary piece and the mandible piece, the attachment member embedded is required to be supported by the maxillary piece and the mandible piece.

The mouthpiece 10 can have a configuration where the maxillary piece 1 and the mandible piece 2 are sandwiched between the first base portion of the maxillary member 3 and the second base portion of the mandible member 4, and the first joint portion and the second joint portion of the joining member 5, respectively, thereby allowing a relatively soft material to be used as the material forming the maxillary piece 1 and the mandible piece 2.

The mouthpiece 10 may have portions of the maxillary piece 1 and the mandible piece 2, other than the portion of the maxillary piece 1, sandwiched between the first base portion and the first joint portion, and the portion of the mandible piece 2, sandwiched between the second base portion and the second joint portion, being formed from the material having a tensile strength of 150 N or more and less than 2000 N or being formed from another material in.

It is preferable in the mouthpiece 10 that the first base portion of the maxillary member 3 is accommodated in the through-hole so as to serve as a depressed portion to the wall surface 1b of the outer wall portion closer to the maxillary, the wall surface 1b closer to the row of teeth. It is also preferable in the mouthpiece 10 that the second base portion of the mandible member 4 is accommodated in the through-hole so as to serve as a depressed portion to the wall surface 2b of the outer wall portion closer to the mandible, the wall surface 2b closer to the row of teeth. Thus, the rear surface 3b or the rear surface 4b is inhibited from being in contact with the gingiva and application of load to the gingiva is suitably suppressed in application of any load to the maxillary member 3 or the mandible member 4, in wearing of the mouthpiece 10.

It is preferable in the mouthpiece 10 that the joining member 5 has a non-step regulation function for regulation of the distance between the maxillary member 3 and the mandible member 4. For example, such a configuration where the joining member 5 has a non-step regulation function may be a configuration where a male screw having a screw thread on the outer surface thereof and a female screw having a screw thread on the inner surface thereof are provided and the distance between the maxillary member 3 and the mandible member 4 can be regulated by the male screw and the female screw. The distance between the maxillary member 3 and the mandible member 4 can be thus regulated, if appropriate in the mouthpiece 10, and fine adjustment in wearing can be made.

When the mouthpiece 10 has a non-step regulation function, the distance between the maxillary member 3 and the mandible member 4 (the distance between the centers) in each of the joining members 5 can be preferably regulated to from 18 mm to 50 mm.

Examples of the joining member 5 include members formed from various materials such as a metal and plastic, and members formed from plastic are preferable because such members can be applied to a metal allergy patient, can achieve a decrease in the weight with the strength thereof being kept, or can reduce a feeling of strangeness in the oral cavity.

Figure 2:
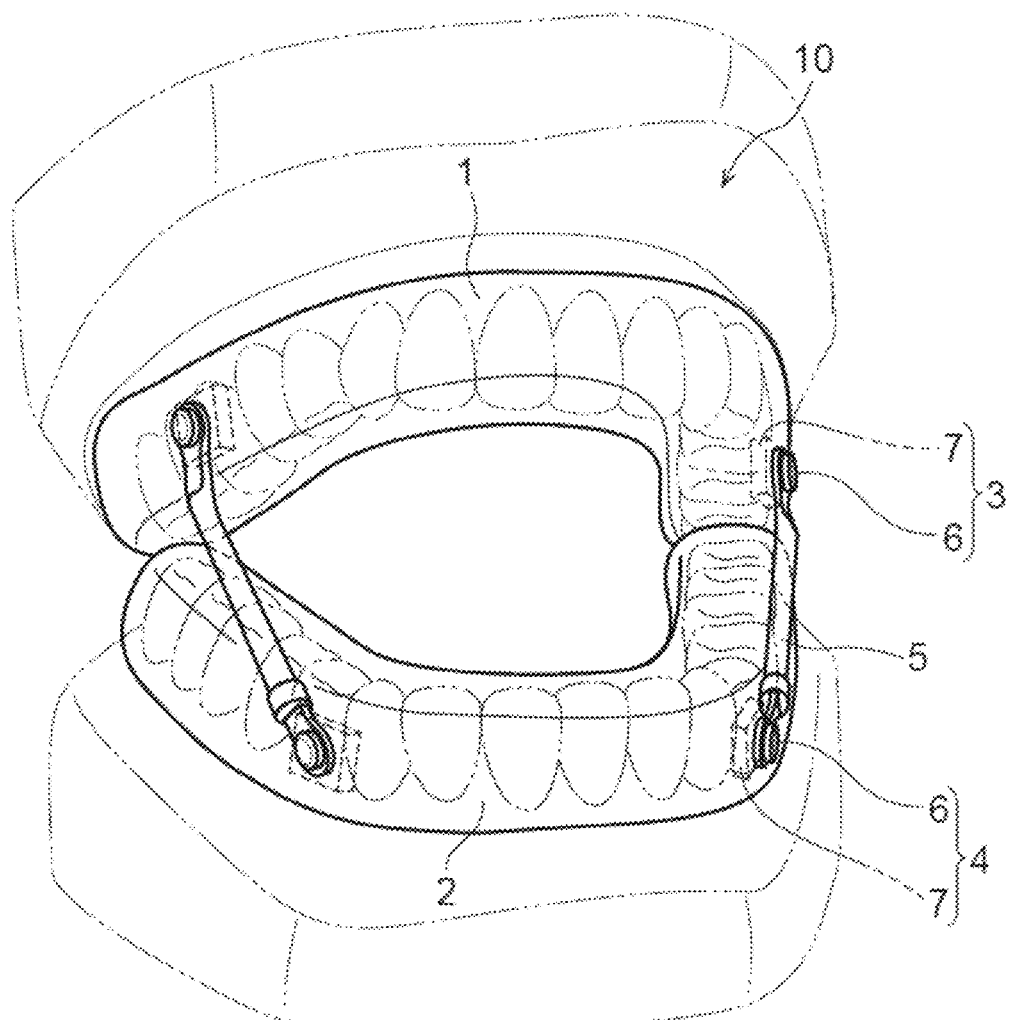
FIG. 2 includes a perspective view illustrating a schematic configuration of a mouthpiece according to one example of the first aspect.

It is preferable in the mouthpiece 10 that a section for insertion into the through-hole of the maxillary piece 1 and attachment of the maxillary member 3 is located more rearward (in other words, closer to the back teeth) than a section for insertion into the through-hole of the mandible piece 2 and attachment of the mandible member 4, when viewed from the center of the row of teeth, as illustrated in FIG. 1 and FIG. 2. That is, the mouthpiece 10 is preferably a push type mouthpiece which pushes the mandible forward in wearing. The mouthpiece 10 is such a push type mouthpiece, to thereby allow the mouth to be more easily opened in wearing, than the case of a pull type mouthpiece described below.

The push type mouthpiece 10 is larger in the force applied to the maxillary member 3 and the mandible member 4 than a pull type mouthpiece, thereby easily causing backlash of the maxillary member 3 and the mandible member 4. The configuration where each of the maxillary piece 1 and the mandible piece 2 is sandwiched, as described above, however, is adopted, thereby allowing the maxillary piece 1 and the mandible piece 2 to be in close contact with the first base portion of the maxillary member 3 and the second base portion of the mandible member 4. Therefore, backlash of the maxillary member 3 and the mandible member 4 is also suitably suppressed even in a case of the push type mouthpiece.

When the mouthpiece 10 is a push type mouthpiece, a section of the maxillary piece 1, attached to the maxillary member 3, preferably corresponds to at least a part of a region corresponding to from the fifth to the eighth of the row of teeth of the maxillary (or from the fifth to the seventh of the row of teeth), and a section of the mandible piece 2, attached to the mandible member 4, preferably corresponds to at least a part of a region corresponding to from the second to the fifth of the row of teeth of the mandible.

A section for insertion into the through-hole of the mandible piece and attachment of the mandible attachment member may be located more rearward than a section for insertion into the through-hole of the maxillary piece and attachment of the maxillary attachment member, when viewed from the center of the row of teeth, in the mouthpiece according to the aspect. That is, the mouthpiece according to the aspect may also be a pull type mouthpiece which pulls the maxillary forward in wearing.

When the mouthpiece according to the aspect is a push type mouthpiece, a section of the mandible piece, to which the mandible attachment member is attached, preferably corresponds to at least a part of a region corresponding from the fifth to the eighth of the row of teeth of the mandible (from the fifth to the seventh of the row of teeth), and a section of the maxillary piece, to which the maxillary attachment member is attached, preferably corresponds to at least a part of a region corresponding from the second to the fifth of the row of teeth of the maxillary.

Figure 3:
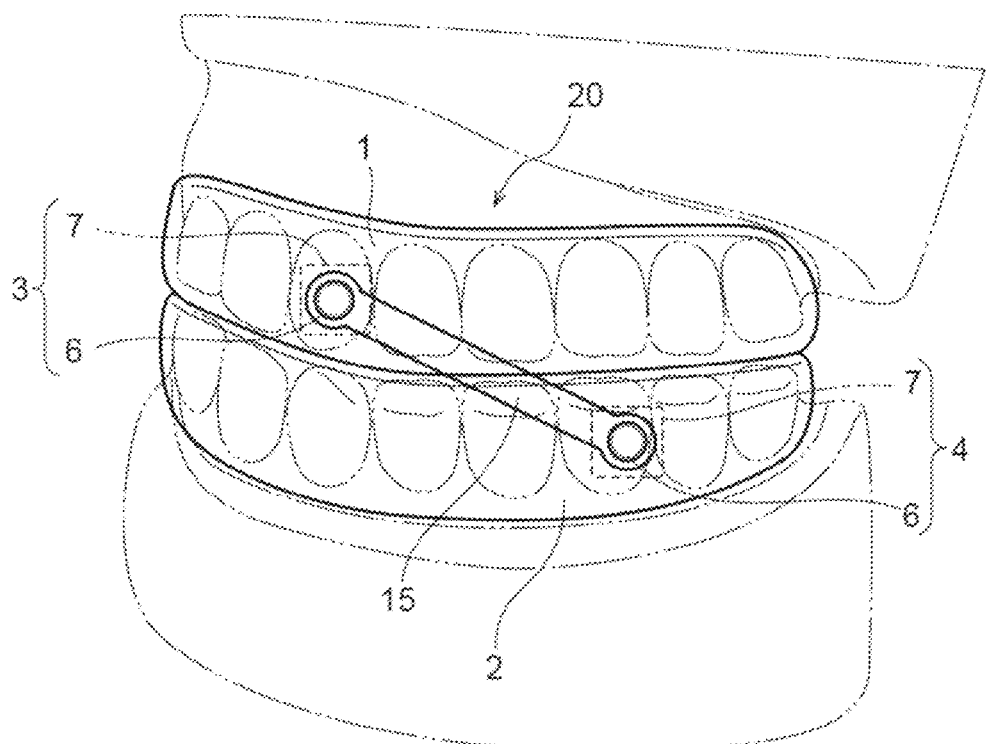
FIG. 3 includes a side view illustrating a schematic configuration of a mouthpiece according to a modification example of the first aspect.
Figure 4:
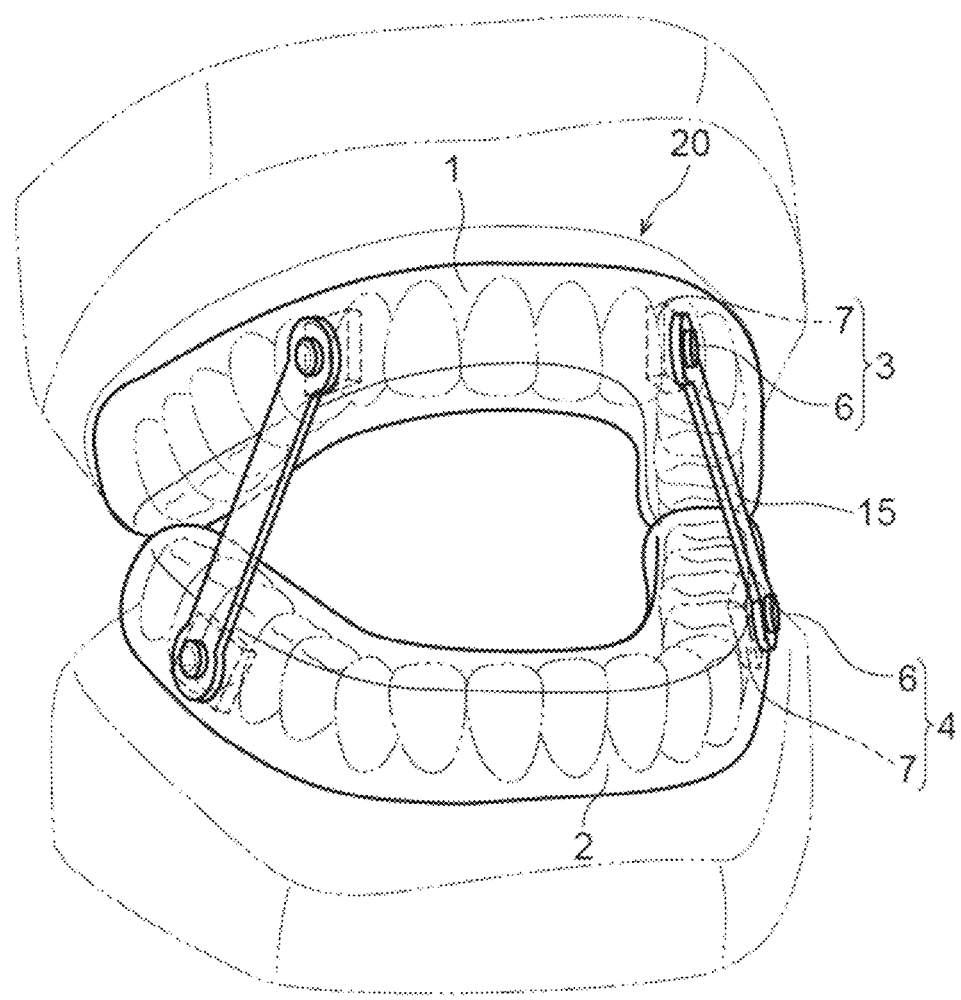
FIG. 4 includes a perspective view illustrating a schematic configuration of a mouthpiece according to a modification example of the first aspect.

A pull type mouthpiece 20 is illustrated in FIG. 3 and FIG. 4. A section for insertion into the through-hole of the mandible piece 2 and attachment of the mandible member 4 is located more rearward than a section for insertion into the through-hole of the maxillary piece 1 and attachment of the maxillary member 3, when viewed from the center of the row of teeth, in the pull type mouthpiece 20.

The mouthpiece 20 includes joining members 15 each having a first joint portion and a second joint portion. The joining members 5 are members which are provided rightward and leftward when viewed from the center of the row of teeth, which are attached to the first attachment portion and the second attachment portion of the fitting member 7 at each of the right and left locations, through the first joint portion and the second joint portion, respectively, and which openably and closably joint the maxillary member 3 and the mandible member 4.

In the mouthpiece 10, the cross section perpendicularly intersecting with the thickness direction (direction from the inside of the piece (the inside of the row of teeth in wearing) towards the outside of the piece (the outside of the row of teeth in wearing)) of the maxillary piece 1 of the first base portion of the maxillary member 3 is preferably at least one of bilaterally symmetric or vertically symmetric, more preferably vertically and bilaterally symmetric.

In the mouthpiece 10, the cross section perpendicularly intersecting with the thickness direction (direction from the inside of the piece (the inside of the row of teeth in wearing) towards the outside of the piece (the outside of the row of teeth in wearing)) of the mandible piece 2 of the second base portion of the mandible member 4 is preferably at least one of bilaterally symmetric or vertically symmetric, more preferably vertically and bilaterally symmetric.

Such cross sections can be at least one of bilaterally symmetric or vertically symmetric, thereby distributing the stress applied to the first base portion of the maxillary member 3 and the stress applied to the second base portion of the mandible member 4, and inhibiting the maxillary member 3 and the mandible member 4 from being broken.

Examples of the shape of each of the cross section of the maxillary member 3 and the cross section of the mandible member 4 include polygons such as triangle, tetragon and pentagon, a round shape, an elliptical shape, and a star shape, and examples of the tetragon include square, rectangle, rhomboid, trapezoid and parallelogram.

The shape of each of the cross section of the maxillary member 3 and the cross section of the mandible member 4 is more preferably vertically and bilaterally symmetric from the viewpoint of stress distribution, and therefore the shape is still more preferably square, rectangle, rhomboid, a round shape, an elliptical shape or the like, and is particularly preferably square, rectangle, rhomboid, an elliptical shape or the like from the viewpoint of inhibiting the maxillary member 3 and the mandible member 4 from being rotated.

The shape of each of the cross section of the maxillary member 3 and the cross section of the mandible member 4 is preferably nonangular and rounded from the viewpoint of inhibiting the maxillary piece 1 or the mandible piece 2 from being damaged by any force applied to the maxillary member 3 or the mandible member 4. When the shape of each of the cross sections is a polygon or a star shape, the vertex where two sides are in contact with each other is preferably nonangular and rounded.

It is preferable in the mouthpiece 10 that the cross section of the maxillary member 3 and the cross section of the mandible member 4 have a rectangular shape or an elliptical shape and the longer side or the longer axis is in parallel with the row of teeth (may also be substantially in parallel therewith). The longer side or the longer axis can be in parallel with the row of teeth, thereby allowing the space for the maxillary member 3 and the mandible member 4 of the maxillary piece 1 and the mandible piece 2 to be sufficiently secured, thereby facilitating the design of the mouthpiece. The longer side or the longer axis may be perpendicular to the row of teeth (may also be substantially perpendicular thereto).

In the mouthpiece 10, the height of each of the cross section of the maxillary member 3 and the cross section of the mandible member 4 (direction perpendicular to the row of teeth and the thickness direction of the piece) is preferably 10 mm, more preferably from 5 mm to 10 mm.

While a production method of the mouthpiece according to the first aspect is hereinafter described, the production method is not particularly limited, and is not intended to be limited to a production method of, for example, a mouthpiece in which the materials of the maxillary piece and the mandible piece can be deformed by suction or the like.

[Production Method 1 of Mouthpiece]

Figure 8:
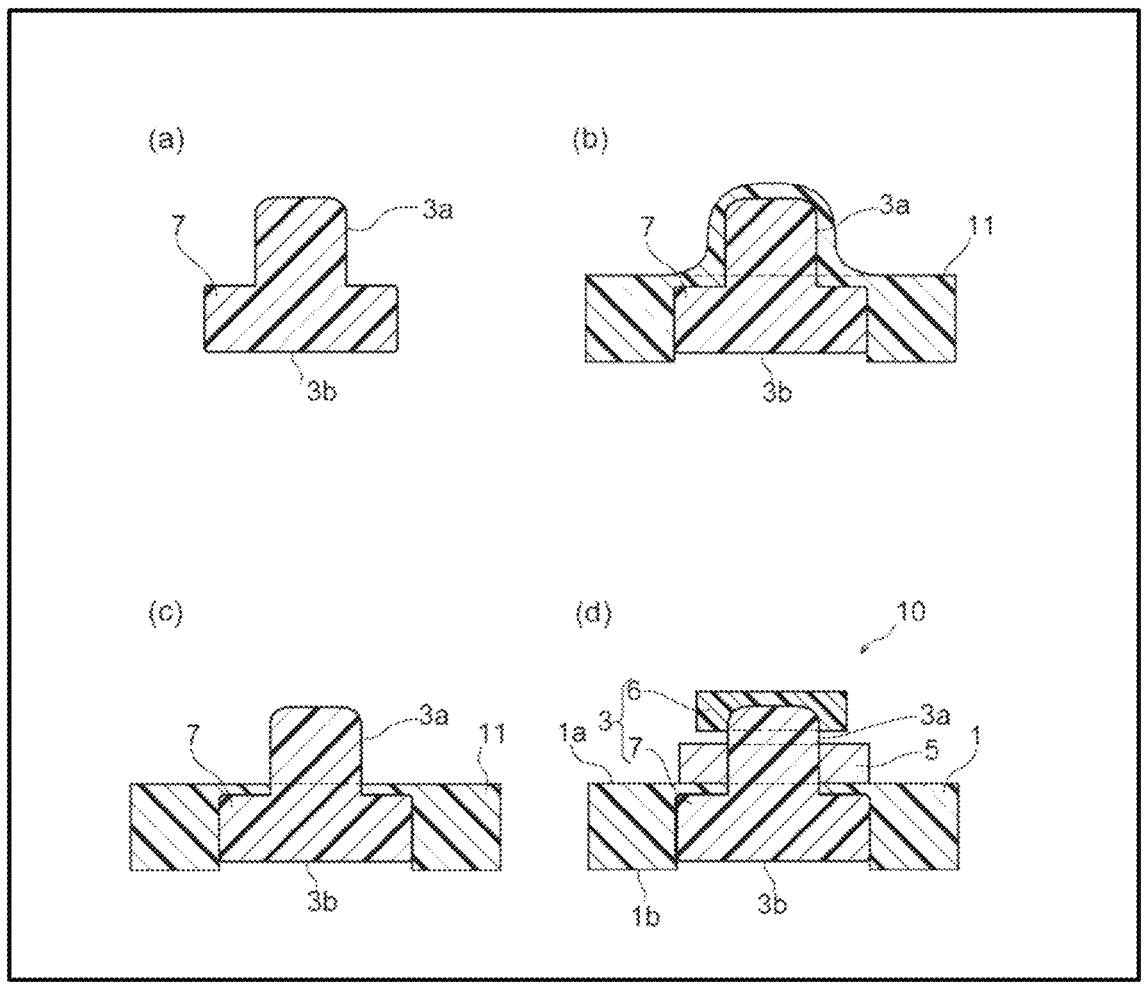
FIG. 8 includes a view illustrating a production method 1 of a mouthpiece according to one example of the first aspect.

A production method 1 of a mouthpiece 10 is described with reference to FIG. 8. As illustrated in FIG. 8(*a*), a fitting member 7 is prepared, and a sheet 11 is contact-bonded by suction, contact-bonded by pressure, or sucked and thereafter contact-bonded to a first attachment portion 3*a* of the fitting member 7, as illustrated in FIG. 8(*b*). A rear surface 3*b* of the fitting member 7 is not covered with the sheet 11 and is exposed, and the rear surface 3*b* of the fitting member 7 is preferably positioned inward over the rear surface of the sheet 11.

As illustrated in FIG. 8(*c*), the sheet 11 with which first attachment portion 3*a* of the fitting member 7 is covered is then removed, to expose the first attachment portion 3*a* from the sheet 11. A tooth profile corresponding to the row of teeth on which the mouthpiece 10 is to be worn is then formed onto the sheet 11, thereby forming a maxillary piece 1. Thus, the fitting member 7 is disposed so that both ends thereof are exposed from the maxillary piece 1. When the mouthpiece 10 to be produced is a push type mouthpiece, the maxillary piece 1 is preferably formed so that a section of the maxillary piece 1, to which the fitting member 7 is attached, corresponds to at least a part of a region corresponding to from the fifth to the eighth of the row of teeth of the maxillary (or from the fifth to the seventh of the row of teeth).

The same operation as above is performed, to thereby allow the fitting member 7 forming the mandible member 4 to be disposed so that both ends of the fitting member 7 are exposed from the mandible piece 2. When the mouthpiece 10 to be produced is a push type mouthpiece, the mandible piece 2 is preferably formed so that a section of the mandible piece 2, to which the fitting member 7 is attached, corresponds to at least a part of a region corresponding to from the second to the fifth of the row of teeth of the mandible.

As illustrated in FIG. 8(*d*), the first attachment portion 3*a* of the fitting member 7 is then fitted into a through-hole provided on a first joint portion of each joining member 5, to attach the joining member 5 to the first attachment portion 3*a*, and thereafter an opening member 6 is fitted in the first attachment portion 3*a*, to provide a maxillary member 3.

A second attachment portion 4*a* of the fitting member 7 is fitted in a through-hole provided on a second joint portion of each joining member 5, to attach the joining member 5 to the second attachment portion 4*a*, and thereafter the opening member 6 is fitted in the second attachment portion 4*a*, to provide a mandible member 4.

[Production Method 2 of Mouthpiece]

Figure 9:
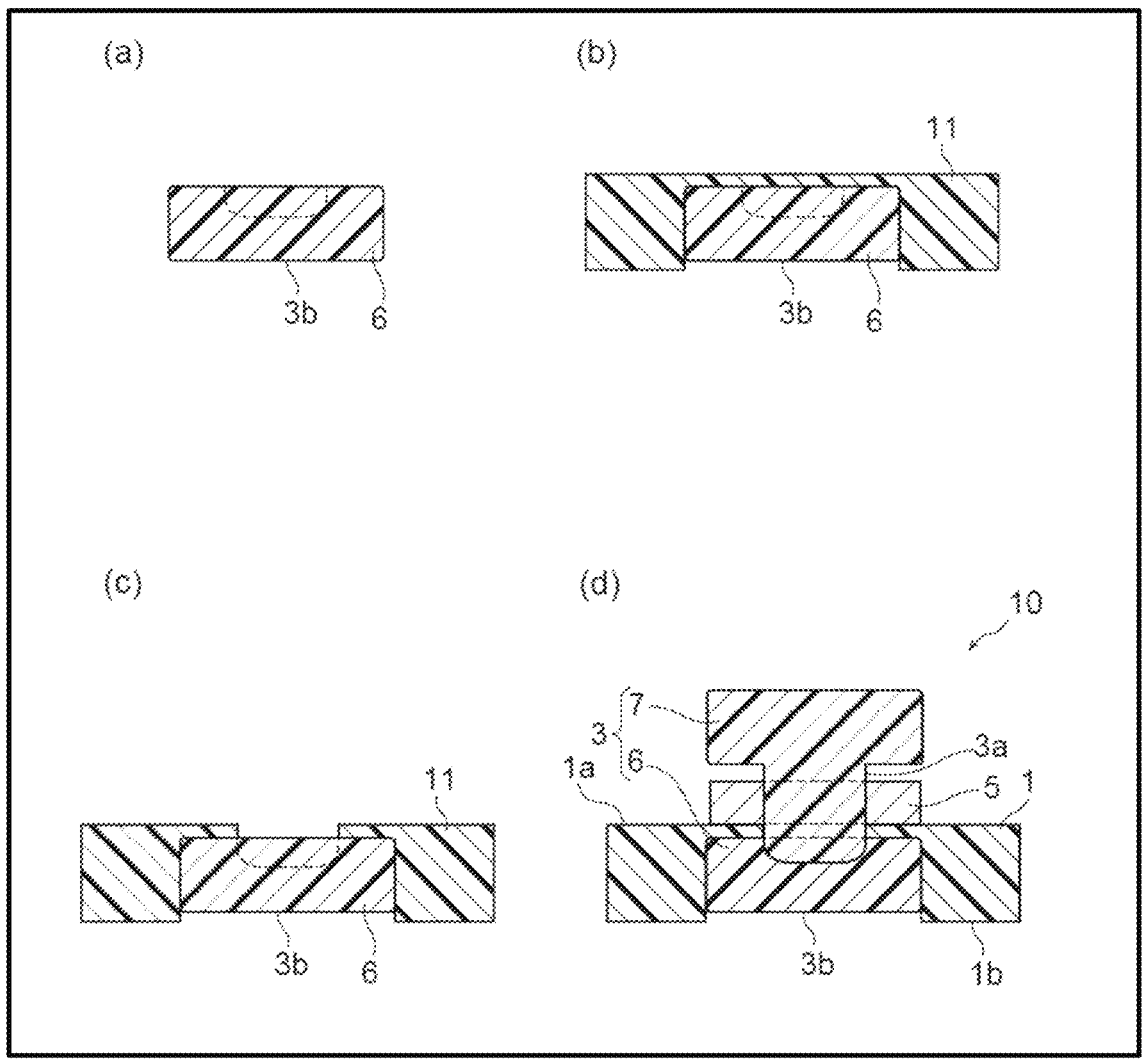
FIG. 9 includes a view illustrating a production method 2 of a mouthpiece according to one example of the first aspect.

A production method 2 of a mouthpiece 10 is specifically described with reference to FIG. 9. An opening member 6 forming the maxillary member 3 is first prepared as illustrated in FIG. 9(*a*), and a sheet 11 to be formed into a maxillary piece 1 is contact-bonded by suction, contact-bonded by pressure, or sucked and thereafter contact-bonded to an opening portion of the opening member 6 (dotted line region in FIG. 9), as illustrated in FIG. 9(*b*). A rear surface 3*b* of the opening member 6 is not covered with the sheet 11 and is exposed, and the rear surface 3*b* of the opening member 6 is preferably positioned inward over the rear surface of the sheet 11, as illustrated in the drawing.

As illustrated in FIG. 9(*c*), the sheet 11 with which the opening portion of the opening member 6 is covered is then removed, to expose the opening portion from the sheet 11. A tooth profile corresponding to the row of teeth on which the mouthpiece 10 is to be worn is then formed onto the sheet 11, thereby forming a maxillary piece 1. Thus, opening member 6 is disposed so that both ends thereof are exposed from the maxillary piece 1. When the mouthpiece 10 to be produced is a push type mouthpiece, the maxillary piece 1 is preferably formed so that a section of the maxillary piece 1, to which the opening member 6 is attached, corresponds to at least a part of a region corresponding to from the fifth to the eighth of the row of teeth of the maxillary (or from the fifth to the seventh of the row of teeth).

The same operation as above is performed, to thereby allow the opening member 6 forming the mandible member 4 to be disposed so that both ends of the opening member 6 are exposed from the mandible piece 2. When the mouthpiece 10 to be produced is a push type mouthpiece, the mandible piece 2 is preferably formed so that a section of the mandible piece 2, to which the opening member 6 is attached, corresponds to at least a part of a region corresponding to from the second to the fifth of the row of teeth of the mandible.

As illustrated in FIG. 9(*d*), a first attachment portion 3*a* of a fitting member 7 is fitted into a through-hole provided on a first joint portion of each joining member 5, to attach the joining member 5 to the first attachment portion 3*a*, and thereafter the opening member 6 is fitted in the first attachment portion 3a, to provide a maxillary member 3.

A second attachment portion 4a of the fitting member 7 is fitted in a through-hole provided on a second joint portion of each joining member 5, to attach the joining member 5 to the second attachment portion 4a, and thereafter the second attachment portion 4a is fitted in the opening member 6, to provide a mandible member 4.

[Production Method 3 of Mouthpiece]

Figure 10:
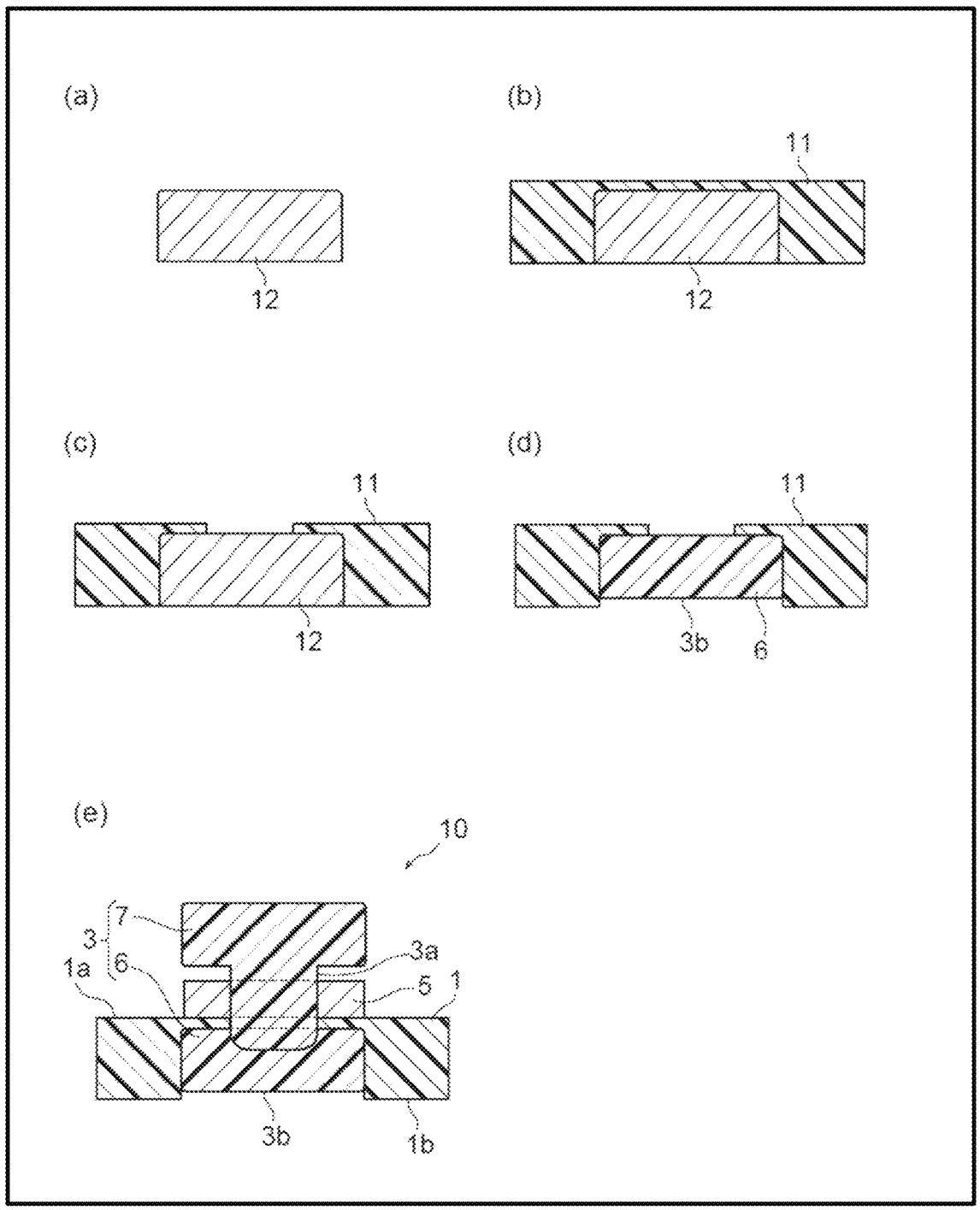
FIG. 10 includes a view illustrating a production method 3 of a mouthpiece according to one example of the first aspect.

A production method 3 of a mouthpiece 10 is described with reference to FIG. 10. A model 12 is prepared instead of the opening member 6 as illustrated in FIG. 10(a), and a sheet 11 to be formed into a maxillary piece 1 is contact-bonded by suction, contact-bonded by pressure, or sucked and thereafter contact-bonded to the morel 12, as illustrated in FIG. 10(b).

As illustrated in FIG. 10(c), the sheet 11 with which the morel 12 is covered is then removed, to expose a part of the surface of the morel 12 from the sheet 11. In a case in which the morel 12 is replaced with an opening member 6 as described below, the sheet 11 with which the morel 12 is covered so that an opening portion of the opening member 6 is exposed is removed.

As illustrated in FIG. 10(d), the morel 12 is then removed, and thereafter the opening member 6 is attached to the sheet 11 so that an opening portion of the opening member 6 is exposed from a portion from which the sheet 11 is removed. The rear surface 3b of the opening member 6 is preferably positioned inward over the rear surface of the sheet 11 as illustrated in the drawing, and therefore, an opening member 6 thinner than the morel 12 (preferably thinner by about 1 mm) is preferably used. The subsequent operation is made in the same manner as in the production method 2 of a mouthpiece, to produce a mouthpiece 10 illustrated in FIG. 10(e).

[Production Method 4 of Mouthpiece]

Figure 11:
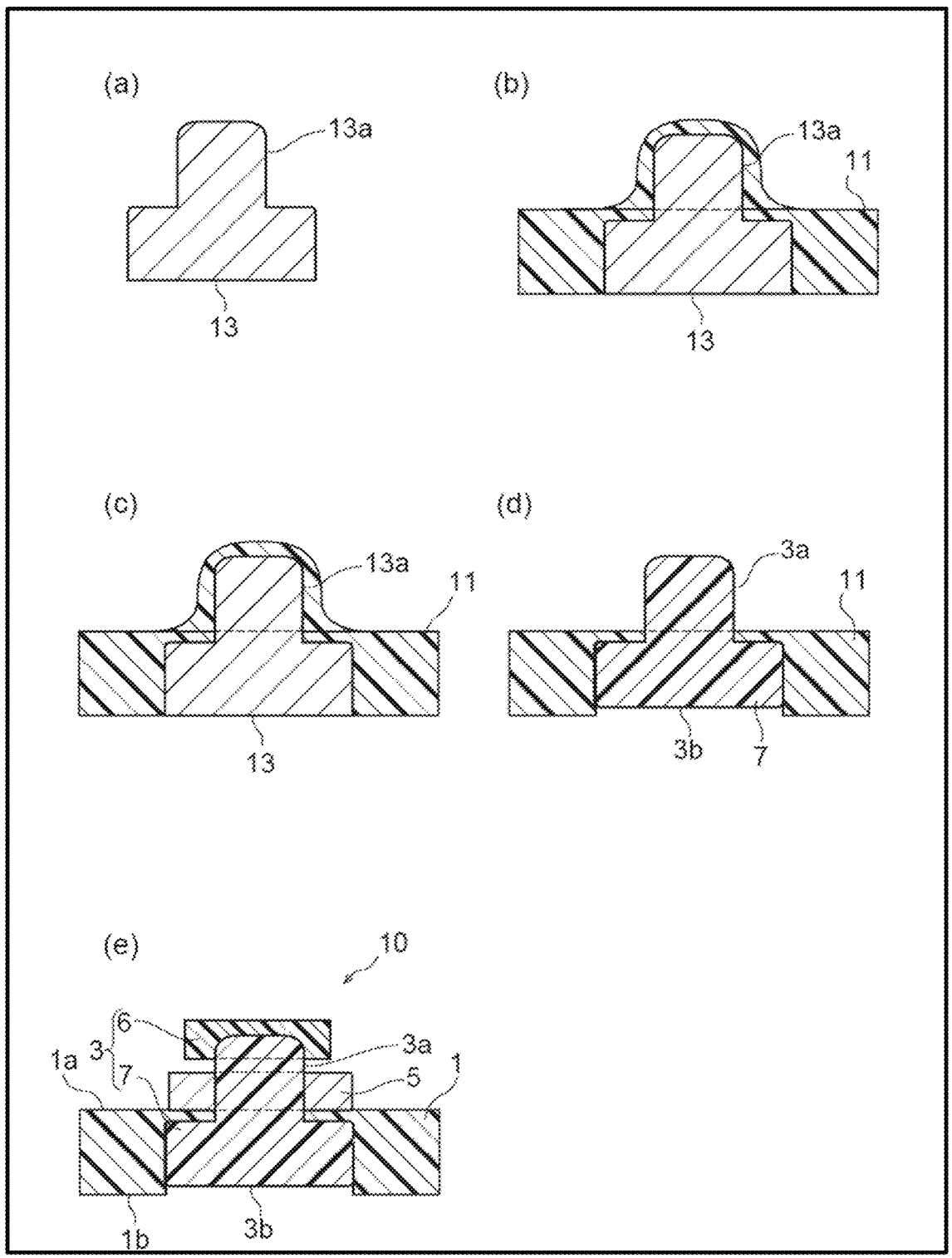
FIG. 11 includes a view illustrating a production method 4 of a mouthpiece according to one example of the first aspect.

A production method 4 of a mouthpiece 10 is specifically described with reference to FIG. 11. A model 13 having a protrusion portion 13a is prepared instead of the fitting member 7 as illustrated in FIG. 11(a), and a sheet 11 to be formed into a maxillary piece 1 is contact-bonded by suction, contact-bonded by pressure, or sucked and thereafter contact-bonded to the model 13, as illustrated in FIG. 11(b).

As illustrated in FIG. 11(c), the sheet 11 with which the model 13 is covered is then removed, to expose the protrusion portion 13a of the model 13 from the sheet 11.

As illustrated in FIG. 11(d), the model 13 is then removed, and thereafter a fitting member 7 is attached to the sheet 11 so that a first attachment portion 3a of the fitting member 7 protrudes and is exposed from a portion from which the sheet 11 is removed. The rear surface 3b of the fitting member 7 is preferably positioned inward over the rear surface of the sheet 11 as illustrated in the drawing, and therefore, a fitting member 7 whose base portion is thinner than the model 13 (preferably thinner by about 1 mm) is preferably used. The subsequent operation is made in the same manner as in the production method 1 of a mouthpiece, to produce a mouthpiece 10 illustrated in FIG. 11(e).

The mouthpiece according to the aspect is not particularly limited in terms of the application thereof, can be used in various applications such as a sporting mouthpiece (mouth guard), a mouthpiece for orthodontics, a mouthpiece for temporomandibular joint syndrome, a mouthpiece (night guard) for bruxism, to be worn during sleep, and a mouthpiece for sleep apnea syndrome, and is particularly suitable for a mouthpiece for sleep apnea syndrome or a mouthpiece for temporomandibular joint syndrome. When the mouthpiece is a mouthpiece for sleep apnea syndrome, such a mouthpiece can be suitably used in order to prevent or at least reduce snoring, bruxism, sleep apnea, and the like.

<Second Aspect>

[Mouthpiece]

Hereinafter, one embodiment of the mouthpiece of the second aspect is described. The description of any matter common with that of the first aspect is omitted (hereinafter, much the same is true on the third and fourth aspects).

The mouthpiece according to the present aspect includes a constituent portion (X) which includes an olefin-based polymer (A) having a repeating unit having 2 or 3 carbon atoms (hereinafter, also referred to as "olefin-based polymer (A)") and which satisfies a bending elastic modulus ($\alpha$) at 23° C., of 80 MPa$\leq\alpha\leq$1000 MPa.

The portion serving as the constituent portion (X) of the mouthpiece according to the aspect is not particularly limited, and the constituent portion (X) is preferably a piece unit to be worn on the row of teeth from the viewpoints of wearing property and polishing workability. The entire piece unit is not necessarily the constituent portion (X), only a part of the piece unit, for example, only a portion to be in contact with the teeth, may be the constituent portion (X), and the entire piece unit is preferably the constituent portion from the viewpoint of molding easiness and the like.

When the constituent portion (X) is a piece unit, the mouthpiece according to the aspect may be a mouthpiece including at least one of a maxillary piece or a mandible piece serving as a piece unit, or may be a mouthpiece (push type or pull type, preferably push type) including a maxillary piece and a mandible piece serving as a piece unit, and other member(s) (for example, joining member for jointing the maxillary piece and the mandible piece).

In the case of a mouthpiece including both a maxillary piece and a mandible piece, at least one of the maxillary piece or the mandible piece is preferably the constituent portion (X), and both the maxillary piece and the mandible piece are preferably the constituent portion (X).

The constituent portion (X) includes an olefin-based polymer (A), thereby suppressing breeding of bacteria caused by one formed by EVA, and also having proper flexibility and hardness. Therefore, the mouthpiece according to the aspect is excellent in wearing property in wearing on the row of teeth and includes a section corresponding to the constituent portion (X) which can be easily processed by polishing, and therefore, for example, can be modified so as to have a shape adapted to the row of teeth and the like of a wearer by polishing of a section corresponding to the constituent portion (X) when the size and the shape of the mouthpiece is not adapted to the row of teeth of the wearer.

The bending elastic modulus ($\alpha$) at 23° C. of the constituent portion (X) is preferably 80 MPa$\leq\alpha\leq$950 MPa, more preferably 85 MPa$\leq\alpha\leq$950 MPa, particularly preferably 90 MPa$\leq\alpha\leq$900 MPa, from the viewpoints of wearing property and polishing workability.

Examples of the olefin-based polymer (A) included in the constituent portion (X) include a homopolymer of ethylene or propylene, having a repeating unit derived from ethylene or propylene, a copolymer of ethylene and propylene, and a copolymer of ethylene or propylene and a monomer other than ethylene and propylene (hereinafter, also referred to as "other monomer").

Examples of such other monomer which can form the olefin-based polymer (A) include linear, branched or cyclic olefin having 4 or more carbon atoms, an aromatic vinyl compound, conjugated diene, unconjugated polyene, and a functionalized vinyl compound.

Examples of the linear or branched α-olefin having 4 or more carbon atoms include linear α-olefins having from 4 to 20 (preferably from 4 to 10) carbon atoms, such as 1-butene, 1-pentene, 1-hexene, 1-octene, 1-decene, 1-dodecene, 1-tetradecene, 1-hexadecene, 1-octadecene and 1-eicosene; and branched α-olefins preferably having from 5 to 20 (more preferably from 5 to 10) carbon atoms, such as 3-methyl-1-butene, 3-methyl-1-pentene, 3-ethyl-1-pentene, 4-methyl-1-pentene, 4,4-dimethyl-1-pentene, 4-methyl-1-hexene, 4,4-dimethyl-1-hexene, 4-ethyl-1-hexene and 3-ethyl-1-hexene.

Examples of the cyclic olefin include compounds having from 4 to 20 (preferably from 5 to 15) carbon atoms, such as cyclopentene, cycloheptene, norbornene, 5-methyl-2-norbornene, tetracyclododecene, vinylnorbornene and vinylcyclohexane.

Examples of the aromatic vinyl compound include styrene; and mono- or polyalkylstyrenes such as α-methylstyrene, o-methylstyrene, m-methylstyrene, p-methylstyrene, o,p-dimethylstyrene, o-ethylstyrene, m-ethylstyrene and p-ethylstyrene.

Examples of the conjugated diene include compounds having from 4 to 20 (preferably from 4 to 10) carbon atoms, such as 1,3-butadiene, isoprene, chloroprene, 1,3-pentadiene, 2,3-dimethylbutadiene, 4-methyl-1,3-pentadiene, 1,3-hexadiene and 1,3-octadiene.

Examples of the unconjugated polyene include compounds having from 5 to 20 (preferably from 5 to 10) carbon atoms, such as 1,4-pentadiene, 1,4-hexadiene, 1,5-hexadiene, 1,4-octadiene, 1,5-octadiene, 1,6-octadiene, 1,7-octadiene, 2-methyl-1,5-hexadiene, 6-methyl-1,5-heptadiene, 7-methyl-1,6-octadiene, 4-ethylidene-8-methyl-1,7-nonadiene, 4,8-dimethyl-1,4,8-decatriene (DMDT), dicyclopentadiene, cyclohexadiene, dicyclooctadiene, ethylenenorbornene, 5-vinylnorbornene, 5-ethylidene-2-norbornene, 5-ethylene-2-norbornene, 5-isopropylidene-2-norbornene, 6-chloromethyl-5-isopropenyl-2-norbornene, 2,3-diisopropylidene-5-norbornene, 2-ethylidene-3-isopropylidene-5-norbornene and 2-propenyl-2,2-norbornadiene.

Examples of the functionalized vinyl compound include hydroxyl group-containing olefin; halogenated olefin; unsaturated carboxylic acids such as acrylic acid, propionic acid, 3-butenoic acid, 4-pentenoic acid, 5-hexenoic acid, 6-heptenoic acid, 7-octenoic acid, 8-nonenoic acid and 9-decenoic acid; unsaturated amines such as allylamine, 5-hexeneamine and 6-hepteneamine; unsaturated acid anhydrides such as (2,7-octadienyl)succinic anhydride, pentapropenyl succinic anhydride, and anhydrides of the unsaturated carboxylic acids; halides of the unsaturated carboxylic acids; and unsaturated epoxy compounds such as 4-epoxy-1-butene, 5-epoxy-1-pentene, 6-epoxy-1-hexene, 7-epoxy-1-heptene, 8-epoxy-1-octene, 9-epoxy-1-nonene, 10-epoxy-1-decene and 11-epoxy-1-undecene.

The hydroxyl group-containing olefin may be an olefin-based compound having a hydroxyl group. The hydroxyl group-containing olefin is preferably a terminal hydroxylated olefin compound.

Examples of the terminal hydroxylated olefin compound include linear hydroxylated α-olefin having from 4 to 20 (preferably from 4 to 10) carbon atoms, such as vinyl alcohol, allyl alcohol, hydroxylated-1-butene, hydroxylated-1-pentene, hydroxylated-1-hexene, hydroxylated-1-octene, hydroxylated-1-decene, hydroxylated-1-dodecene, hydroxylated-1-tetradecene, hydroxylated-1-hexadecene, hydroxylated-1-octadecene and hydroxylated-1-eicosene; and branched hydroxylated α-olefin preferably having from 5 to 20 (more preferably from 5 to 10) carbon atoms, such as hydroxylated-3-methyl-1-butene, hydroxylated-4-methyl-1-pentene, hydroxylated-3-methyl-1-pentene, hydroxylated-3-ethyl-1-pentene, hydroxylated-4,4-dimethyl-1-pentene, hydroxylated-4-methyl-1-hexene, hydroxylated-4,4-dimethyl-1-hexene, hydroxylated-4-ethyl-1-hexene and hydroxylated-3-ethyl-1-hexene.

Examples of the halogenated olefin include linear halogenated α-olefin having from 4 to 20 (preferably from 4 to 10) carbon atoms, such as halogenated-1-butene, halogenated-1-pentene, halogenated-1-hexene, halogenated-1-octene, halogenated-1-decene, halogenated-1-dodecene, halogenated-1-tetradecene, halogenated-1-hexadecene, halogenated-1-octadecene and halogenated-1-eicosene; and branched halogenated α-olefin preferably having from 5 to 20 (more preferably from 5 to 10) carbon atoms, such as halogenated-3-methyl-1-butene, halogenated-4-methyl-1-pentene, halogenated-3-methyl-1-pentene, halogenated-3-ethyl-1-pentene, halogenated-4,4-dimethyl-1-pentene, halogenated-4-methyl-1-hexene, halogenated-4,4-dimethyl-1-hexene, halogenated-4-ethyl-1-hexene and halogenated-3-ethyl-1-hexene.

The olefin-based polymer (A) included in the constituent portion (X) preferably has a structural unit derived from a siloxane structure. The olefin-based polymer (A) included in the constituent portion (X) can have not only a repeating unit having 2 or 3 carbon atoms, but also a structural unit derived from a siloxane structure, resulting in enhancements in water repellency, oil repellency and abrasive resistance.

The olefin-based polymer (A) having a structural unit derived from a siloxane structure can be obtained by, for example, copolymerizing an olefin-based monomer having 2 or 3 carbon atoms (ethylene or propylene) and a monomer having a siloxane structure (—SiO—). Alternatively, the olefin-based polymer (A) having a repeating unit having 2 or 3 carbon atoms and having a structural unit derived from a siloxane structure can be obtained by adding a monomer having a siloxane structure to, or crosslinking a polymer having a siloxane structure with an olefin-based polymer having a repeating unit having 2 or 3 carbon atoms.

A commercially available product can be used as the olefin-based polymer (A) having a repeating unit having 2 or 3 carbon atoms and a structural unit derived from a siloxane structure, and for example, Exfola (registered trademark, produced by Mitsui Chemicals, Inc.), GENIOPLAST (produced by wacker asahikasei silicone co., ltd.), or Clinbell (produced by Fuji Chemical Industries, Ltd.) can be used.

The constituent portion (X) may be formed using only an olefin-based polymer (A-1) having a repeating unit having 2 or 3 carbon atoms and having no structural unit derived from a siloxane structure, may be formed using only an olefin-based polymer (A-2) having a repeating unit having 2 or 3 carbon atoms and a structural unit derived from a siloxane structure, may be formed using a resin where the olefin-based polymer (A-1) and the olefin-based polymer (A-2) are blended, or may be formed by blending at least one of the olefin-based polymer (A-1) or the olefin-based polymer (A-2), and another resin component (B), as a resin component, as long as the constituent portion (X) satisfies a relationship of a bending elastic modulus (α) at 23° C., of 80 MPa≤α≤1000 MPa.

The thickness of the constituent portion (X) is preferably from 0.3 to 5.0 mm when the constituent portion (X) is a piece unit, while the thickness varies depending on a portion of the mouthpiece. When the thickness of the constituent portion (X) is 0.3 mm or more, the constituent portion (X) is inhibited from being broken even if subjected to application of a strong load by the bruxism and the like in wearing of the mouthpiece. On the other hand, when the thickness of the constituent portion (X) is 5.0 mm or less, a foreign-body feeling in the oral cavity in wearing of the mouthpiece is kept down, and favorable wear feeling is obtained. The thickness of the constituent portion (X) is more preferably from 0.4 mm to 4.5 mm, still more preferably from 0.5 mm to 4.0 mm, from such viewpoints.

The constituent portion (X) preferably satisfies $0\% \leq \beta \leq 1.0\%$, more preferably satisfies $0\% \leq \beta \leq 0.5\%$, as the water absorption rate ($\beta$) when dried at 50° C. for 24 hours and then immersed in a water bath at 37° C. for 24 hours.

The water absorption rate ($\beta$) is a value calculated according to the following Formula (I) where the mass of the constituent portion (X) before immersion in a water bath at 37° C. immediately after drying at 50° C. for 24 hours is designated as W0 and the mass of the constituent portion (X) immediately after immersion in a water bath at 37° C. for 24 hours is designated as W1.

$$\text{Water absorption rate } (\beta) = [(W1-W0)/W0] \cdot 100(\%) \qquad (I)$$

When the water absorption rate ($\beta$) of the constituent portion is 1.0% or less, wear feeling can be inhibited from being lost due to water absorption and expansion of the constituent portion (X) by beverage, saliva or the like when the mouthpiece is washed with a washing liquid containing water, is worn by a wearer, and the like.

The water absorption rate ($\beta$) can be kept down by a repeated structure of olefin.

The constituent portion (X) may be a monolayer, or may have a layered structure where two or more layers are layered. When the constituent portion (X) has such a layered structure, at least one layer may include the olefin-based polymer (A) and satisfy a relationship of a bending elastic modulus ($\alpha$) at 23° C., of 80 MPa$\leq \alpha \leq$1000 MPa, as the entire laminated body forming the constituent portion (X), and/or the constituent portion (X) may have a layered structure including a layer (LI) which satisfies a bending elastic modulus ($\alpha$1) at 23° C., of 5 MPa$\leq \alpha 1 \leq$100 MPa (hereinafter, also referred to as "LI layer") and a layer (LO) which satisfies a bending elastic modulus ($\alpha$2) at 23° C., of 200 MPa$\leq \alpha \leq$1500 MPa (hereinafter, also referred to as "LO layer"). The constituent portion (X) can have such a layered structure including the LI layer and the LO layer each having the above bending elastic modulus, thereby providing a configuration where each of wearing property and polishing workability differs between a section of the mouthpiece, to be in contact with the teeth, and a section of the mouthpiece, to be in contact with the tongue and the lip, in wearing of the mouthpiece.

When the constituent portion (X) has the layered structure including the LI layer and the LO layer each having the above bending elastic modulus, the layer (LI) is preferably exposed at at least a part of an outermost surface of the constituent portion (X).

The LI layer has flexibility, and therefore hardly causes any pain to a wearer even in contact with the gums in wearing, as along as the LI layer is exposed as an outermost surface of the constituent portion (X), to be in contact with the teeth (closer to the inner layer). On the other hand, when the L layer is exposed as an outermost surface of the constituent portion (X), to be in contact with the tongue and the lip (closer to the outer layer), a wearer hardly has a feeling of strangeness and pain even if the tongue and the lip thereof is touched.

A surface of the LI layer may be thinly coated with a hydrophilic coating or a hydrophobic coating.

Examples of the hydrophilic coating include LAMBIC (produced by OSAKA ORGANIC CHEMICAL INDUSTRY LTD.). Examples of the hydrophobic coating include PIKASSHU (produced by PIKASSHU Corporation).

While the mouthpiece preferably has a high strength as a whole, for example, so as not to be broken by the bruxism and the like in wearing, the mouthpiece preferably has flexibility which allows a surface of the mouthpiece, the surface being in contact with the teeth in wearing on the row of teeth, to be deformed according to the shape of the row of teeth. Therefore, when the constituent portion (X) has the layered structure including the LI layer and the LO layer each having the above bending elastic modulus, it is preferable that the constituent portion (X) is a portion to be in contact with the teeth in wearing of the mouthpiece on the row of teeth and the LI layer is exposed at at least a part of a surface of the portion to be in contact with the teeth from the viewpoints of comfort and wear feeling. For example, an inner layer (which is to be in contact with the teeth) of the constituent portion (X) may be the LI layer, and an outer layer (which is to be in contact with the tongue and the lip) thereof may be the LO layer.

The bending elastic modulus ($\alpha$1) at 23° C. of the LI layer is preferably 5 MPa$\leq \alpha 1 \leq$95 MPa, more preferably 10 MPa$\leq \alpha 1 \leq$95 MPa, particularly preferably 10 MPa$\leq \alpha 1 \leq$90 MPa, from the above viewpoints.

The LI layer which satisfies a bending elastic modulus ($\alpha$1) at 23° C., of 5 MPa$\leq \alpha 1 \leq$100 MPa, may be formed using a commercially available product, and examples of such a commercially available product include TAFMER DF-810 (Mitsui Chemicals, Inc.), NOTIO SN-0285 (produced by Mitsui Chemicals, Inc.), Vistamaxx 6102 (produced by Exxon Mobil Corporation) and Zeras (produced by Mitsubishi Chemical Corporation).

On the other hand, the bending elastic modulus ($\alpha$2) at 23° C. of the LO layer is preferably 500 MPa$\leq \alpha \leq$1500 MPa, more preferably 700 MPa$\leq \alpha 2 \leq$1300 MPa, particularly preferably 800 MPa$\leq \alpha 2 \leq$1200 MPa.

The LO layer which satisfies a bending elastic modulus ($\alpha$2) at 23° C., of 200 MPa$\leq \alpha 2 \leq$1500 MPa, may be formed using a commercially available product, and examples of such a commercially available product include Prime Polypro F327 (produced by Prime Polymer Co., Ltd.), NOVATEC HD HJ590 N (produced by Japan Polyethylene Corporation) and WELNEX (produced by Japan Polypropylene Corporation).

When the constituent portion (X) has the layered structure including the LI layer and the LO layer each having the above bending elastic modulus, at least one layer of the LI layer and the LO layer may include the olefin-based polymer (A), but both the LI layer and the LO layer preferably include the olefin-based polymer (A) because, if the kinds of the resins of the LI layer and the LO layer are different, the difference in thermal expansion rate can cause peeling to easily occur and thus restrict the molding temperature in production of the mouthpiece. In such a case, even if an olefin-based polymer (A-I) included in the LI layer and an olefin-based polymer (A-O) included in the LO layer are different in the molecular weight and the structure, both the olefin-based polymers can be each an "olefin-based polymer having a repeating unit having 2 or 3 carbon atoms", thereby ensuring a high close contactability.

The LI layer and the LO layer may be layered with an adhesion layer being interposed therebetween. When the LI layer and the LO layer are layered with an adhesion layer being interposed therebetween, any of various known adhesives can be used in the adhesion layer. Examples include a sticky adhesive, a pressure-sensitive adhesive, a photo-curable adhesive and a hot-melt adhesive. Examples of such an adhesive include an acrylic adhesive, a urethane adhesive, an epoxy adhesive, a polyester adhesive, a polyvinyl alcohol adhesive, a polyolefin adhesive, a modified-polyolefin adhesive, a polyvinylalkylether adhesive, a rubber adhesive, a vinyl chloride-vinyl acetate adhesive, a styrene-butadiene-styrene copolymer (SBS copolymer) adhesive, an adhesive of a hydrogenated product thereof (SEBS copolymer), adhesives of ethylenes such as an ethylene-vinyl acetate copolymer and an ethylene-styrene copolymer, and adhesives of acrylates such as an ethylene-methyl methacrylate copolymer, an ethylene-methyl acrylate copolymer, an ethylene-ethyl methacrylate copolymer and an ethylene-ethyl acrylate copolymer, and are not particularly limited as long as adhesiveness, transparency and processability are favorable.

The LI layer and the LO layer may be bonded by heat-sealing.

[Sheet for Production of Mouthpiece Piece Unit]

The sheet for production of a mouthpiece piece unit, according to the aspect, is a sheet for forming the constituent portion (X).

The method of producing the sheet for production of a mouthpiece piece unit, according to the aspect, is not particularly limited, and the sheet is formed by processing a composition (X) including the olefin-based polymer (A) and also, if necessary, an additive such as a softener, into a sheet shape, by any molding method such as extrusion molding, calender molding, press molding, injection molding, vacuum molding, pressure forming or vacuum pressure forming.

When the sheet has a layered structure, for example, a layered sheet may be obtained by co-extruding a composition forming each layer, or a layered sheet may be obtained by forming a sheet of a monolayer forming each layer, and stacking and heat-pressing each layer. A layered sheet may also be obtained by applying the above-described adhesive to at least one sheet to be layered, and bonding the resultant.

(Softener)

A softener may be, if necessary, compounded to the composition (X). A conventionally known softener can be used as the softener. Examples include petroleum-based substances such as process oil, lubricant oil, paraffin, liquid paraffin, polyethylene wax, polypropylene wax, petroleum asphalt and vaseline; coal tars such as coal tar and coal tar pitch; fatty oils such as castor oil, flaxseed oil, rapeseed oil, soybean oil and palm oil; waxes such as tall oil, beewax, carnauba wax and lanolin; fatty acids such as ricinoleic acid, palmitic acid, stearic acid, 12-hydroxylated stearic acid, montanic acid, oleic acid and erucic acid, and metal salts thereof; synthetic polymers such as a petroleum resin, a coumarone-indene resin and atactic polypropylene; ester-based compounds such as dioctyl phthalate, dioctyl adipate and dioctyl sebacate, and other microcrystalline wax and liquid polybutadiene or a modified product or hydrogenated product thereof; and liquid Thiokol.

(Other Additives)

Additives such as various weather stabilizers, heat-resistant stabilizers, antioxidants, ultraviolet absorbers, antistatic agents, antislip agents, anti-blocking agents, anti-fogging agents, nucleating agents, lubricants, pigments, dyes, anti-aging agents, hydrochloric acid absorbers, inorganic or organic fillers, organic or inorganic foaming agents, crosslinking agents, co-crosslinking agents, crosslinking aids, gluing agents and flame retardants may be, if necessary, compounded in the composition (X).

Specific examples of such additives include a phenolic stabilizer, 2,6-di-t-butyl-p-cresol, tetrakis[ethylene-3-(3,5-di-t-butyl-4-hydroxyphenyl)propionate]methane, 4,4'-butylidenebis(6-t-butyl-m-cresol), tocopherols, ascorbic acid, dilauryl thiodipropionate, a phosphoric acid-based stabilizer, fatty acid monoglyceride,
N,N-[bis-2-hydroxyethyl]alkylamine,
2-(2'-hydroxy-3',5'-di-t-butylphenyl)-5-chlorobenzotriazole, calcium stearate, magnesium oxide, magnesium hydroxide, alumina, aluminum hydroxide, silica, clay, plaster, glass fiber, titania, calcium carbonate and carbon black.

[Production Method of Mouthpiece]

The mouthpiece according to the aspect can be obtained by, for example, hot forming the sheet for production of a mouthpiece piece unit.

The mouthpiece according to the aspect can be produced by the same method as that of a conventional mouthpiece, for example, the method described in WO 2002/98521, JP-A No. 2010-131181, or the like, except that the sheet for production of a piece unit, having the above-described material, physical properties and structure, is used as the material.

The production method of a mouthpiece of the aspect includes a step of hot forming the sheet for production of a mouthpiece piece unit, to provide a mouthpiece piece unit (hereinafter, also referred to as "hot forming step").

Examples of the hot forming step include a step of heating the sheet for production of a mouthpiece piece unit until the sheet is softened, to produce a mouthpiece along with a row of teeth model or a jaw model; and a step of producing a depression-shaped mold by use of a row of teeth model or a jaw model, and injecting the sheet for production of a mouthpiece piece unit into the mold, to produce a mouthpiece. The production method of a mouthpiece of the aspect may include any step other than the hot forming step.

Examples of such other step include a step (polishing and working step) of polishing and working the piece unit obtained in the hot forming step. In the polishing and working step, for example, the piece unit is polished and worked so as to be adapted to the state in the oral cavity, for example, the row of teeth of a wearer. The piece unit is obtained by hot forming the sheet for production of a mouthpiece piece unit, and therefore is excellent in polishing workability.

When a mouthpiece including a maxillary piece and a mandible piece is produced, the production method of a mouthpiece of the embodiment may include a hot forming step of producing the maxillary piece and a hot forming step of producing the mandible piece.

When a mouthpiece including a maxillary piece, a mandible piece and each joining member is produced, the production method of a mouthpiece of the embodiment may include a hot forming step of producing the maxillary piece, a hot forming step of producing the mandible piece, and a step of attaching each joining member to the maxillary piece and the mandible piece.

<Third Aspect>

[Mouthpiece]

Hereinafter, one embodiment of the mouthpiece of the third aspect is described.

The mouthpiece of the present aspect is a mouthpiece to be worn on the row of teeth, wherein the mouthpiece has a layered structure including a layer (A) closer to the row of teeth in wearing of the mouthpiece on the row of teeth and a layer (B) layered on the layer (A) and disposed opposite to the row of teeth in the wearing when viewed from the layer (A), the layer (A) contains at least one elastomer selected from the group consisting of an acrylic thermoplastic elastomer and a polyester-based thermoplastic elastomer, the layer (B) contains at least one polymer selected from the group consisting of poly(meth)acrylate and polyester, the adhesion strength between the layer (A) and the layer (B) is 30 MPa or more, the bending elastic modulus of the layer (A) is from 50 MPa to 300 MPa, the bending elastic modulus of the layer (B) is higher than the bending elastic modulus of the layer (A), and the difference between the bending elastic modulus of the layer (A) and the bending elastic modulus of the layer (B) (namely, the absolute value of the difference; much the same is true on the following.) is from 1000 MPa to 3000 MPa.

The mouthpiece of the aspect is easy in production, and is excellent in wear feeling and durability. The reason why such an effect is exerted is presumed as follows.

It is considered that the bending elastic modulus of the layer (A) to be positioned closer to the row of teeth in wearing is within the above range, thereby giving a moderate feeling of hardness, which is not too hard and not too soft to a wearer, resulting in an enhancement in wear feeling in the aspect.

It is considered that the bending elastic modulus of the layer (A) is easily achieved by allowing the layer (A) to include at least one elastomer selected from the group consisting of an acrylic thermoplastic elastomer and a polyester-based thermoplastic elastomer.

It is also considered that the adhesion strength between the layer (A) and the layer (B) can be 30 MPa or more, to thereby allow for wearing with the layered structure including the layer (A) and the layer (B) being maintained, resulting in an enhancement in wear feeling, in the embodiment.

It is considered that the adhesion strength between the layer (A) and the layer (B) is easily achieved by allowing the layer (A) to contain the elastomer and the layer (B) to contain at least one polymer selected from the group consisting of poly(meth)acrylate and polyester.

It is also considered that the bending elastic modulus of the layer (B) is higher than the bending elastic modulus of the layer (A) and the difference between the bending elastic modulus of the layer (A) and the bending elastic modulus of the layer (B) is from 1000 MPa to 3000 MPa, resulting in an enhancement in durability, in the embodiment.

It is considered that the difference in the bending elastic modulus between the layer (A) and the layer (B) is achieved by allowing the layer (A) to contain the elastomer and the layer (B) to contain at least one polymer selected from the group consisting of poly(meth)acrylate and polyester.

In the embodiment, a thermoplastic elastomer is used as the material of the layer (A), thereby facilitating hot forming into a mouthpiece shape. The mouthpiece of the embodiment is thus easily produced.

The layer (A) is a layer positioned closer to the row of teeth in wearing of the mouthpiece on the row of teeth. The bending elastic modulus of the layer (A) is from 50 MPa to 300 MPa, and is preferably from 100 MPa to 250 MPa, more preferably from 100 MPa to 200 MPa from the viewpoint of a more enhancement in wear feeling.

The layer (A) contains at least one elastomer selected from the group consisting of an acrylic thermoplastic elastomer and a polyester-based thermoplastic elastomer.

The layer (A) may include any component other than such at least one elastomer.

Such at least one elastomer selected from the group consisting of an acrylic thermoplastic elastomer and a polyester-based thermoplastic elastomer is preferably a block copolymer including a hard block and a soft block.

In the block copolymer, the glass transition temperature (Tg) of the hard block is preferably higher than the glass transition temperature (Tg) of the soft block.

The Tg of the hard block is preferably from 30° C. to 200° C., more preferably from 60° C. to 140° C., particularly preferably from 60° C. to 120° C.

The Tg of the soft block is preferably from −100° C. to 0° C., more preferably from −80° C. to −20° C., particularly preferably from −40° C. to −50° C.

Both the hard block and the soft block in the acrylic thermoplastic elastomer as the block copolymer preferably have an alkyl (meth)acrylate unit derived from alkyl (meth)acrylate.

The number of carbon atom(s) in the alkyl portion of the alkyl (meth)acrylate unit in the soft block (hereinafter, also referred to as "number of carbon atom(s) C2") is here preferably larger than the number of carbon atom(s) in the alkyl portion of the alkyl (meth)acrylate unit in the hard block (hereinafter, also referred to as "number of carbon atom(s) C1").

The number of carbon atom(s) in the alkyl portion of the alkyl (meth)acrylate unit in the hard block (the number of carbon atom(s) C1) is preferably from 1 to 6, more preferably from 1 to 3, still more preferably 1 or 2, particularly preferably 1 (namely, the alkyl (meth)acrylate unit is a methyl (meth)acrylate unit).

The alkyl (meth)acrylate unit in the hard block is preferably an alkyl methacrylate unit. The alkyl (meth)acrylate unit in the hard block is particularly preferably a methyl methacrylate unit.

The hard block of the polyester-based thermoplastic elastomer as the block copolymer preferably includes a structural unit having an ester structure.

The number of carbon atom(s) in the alkyl portion of the alkyl (meth)acrylate unit in the soft block (the number of carbon atom(s) C2) may be larger than the number of carbon atom(s) C1.

The difference between the number of carbon atom(s) C1 and the number of carbon atom(s) C2 is preferably 1 or more, more preferably from 1 to 6, still more preferably from 2 to 5, particularly preferably from 2 to 4.

The alkyl (meth)acrylate unit in the soft block is preferably an alkyl acrylate unit. The alkyl (meth)acrylate unit in the soft block is particularly preferably a butyl acrylate unit.

The soft block of the polyester-based thermoplastic elastomer as the block copolymer preferably includes a structural unit having an ester polyol structure.

The ratio of the mass of the hard block to the total mass of the hard block and the soft block in the block copolymer is selected, if appropriate so that the bending elastic modulus of the layer (A) is from 50 MPa to 300 MPa, and the ratio is preferably from 5% by mass to 95% by mass, more preferably from 10% by mass to 90% by mass, particularly preferably from 15% by mass to 85% by mass.

The ratio of the total mass of the hard block and the soft block to the total amount of the block copolymer in the block copolymer is preferably from 80% by mass to 100% by mass, more preferably from 90% by mass to 100% by mass.

The mass average molecular weight (Mw) of the acrylic thermoplastic elastomer is selected, if appropriate so that the bending elastic modulus of the layer (A) is from 50 MPa to 300 MPa, and the Mw is preferably from 10000 to 1000000, more preferably from 20000 to 800000, particularly preferably from 50000 to 500000.

When the acrylic thermoplastic elastomer is the block copolymer, the mass average molecular weight (Mw) of the hard block is selected, if appropriate so that the bending elastic modulus of the layer (A) is from 50 MPa to 300 MPa, and the Mw is preferably from 10000 to 1000000, more preferably from 20000 to 800000, particularly preferably from 50000 to 500000.

When the acrylic thermoplastic elastomer is the block copolymer, the mass average molecular weight (Mw) of the soft block is selected, if appropriate so that the bending elastic modulus of the layer (A) is from 50 MPa to 300 MPa, and the Mw is preferably from 10000 to 1000000, more preferably from 2000 to 800000, particularly preferably from 50000 to 500000.

The mass average molecular weight (Mw) of the polyester-based thermoplastic elastomer, and the mass average molecular weight (Mw) of the hard block and the mass average molecular weight (Mw) of the soft block in the case of the polyester-based thermoplastic elastomer as the block copolymer are also the same as in the case of the acrylic thermoplastic elastomer.

The mass average molecular weight (Mw) herein refers to a value measured with gel permeation chromatograph (GPC) according to the following GPC measurement method.

GPC measurement apparatus—LC-10AD manufactured by Shimadzu Corporation

Column—Shodex K-806L 30 cm×2 columns

Sample preparation—a polymer to be measured is dissolved in a solvent (tetrahydrofuran) at room temperature (from 20° C. to 30° C.), to prepare a sample solution having a concentration of 0.1% (w/v).

Measurement conditions—100 µL of the sample solution is introduced to the column in conditions of a mobile phase (for example, tetrahydrofuran), a column temperature of 40° C. and a flow rate of 1.0 mL/min.

The sample concentration in the sample solution separated by the column is measured with a differential refractometer (RI-101). The universal calibration curve of a polymethyl methacrylate standard sample is created, and the mass average molecular weight (Mw) of a polymer component is calculated.

Analysis may be made using data processing software Empower 2 (manufactured by Waters).

The content of the acrylic thermoplastic elastomer or the polyester-based thermoplastic elastomer with respect to the total amount of the layer (A) is preferably from 50% by mass to 100% by mass, more preferably from 60% by mass to 100% by mass, particularly preferably from 80% by mass to 100% by mass.

The polyester-based thermoplastic elastomer may be an aliphatic polyester crosslinked, described in JP-A No. H011-181034.

An aliphatic polyester to be crosslinked (aliphatic polyester before crosslinking) may be a polycondensate of aliphatic unsaturated polybasic acid or a mixture of aliphatic unsaturated polybasic acid and aliphatic saturated polybasic acid, and aliphatic polyhydric alcohol.

The aliphatic polyester to be crosslinked may be a polycondensate of an aliphatic unsaturated polybasic acid or a mixture of aliphatic unsaturated polybasic acid and aliphatic saturated polybasic acid, aliphatic polyhydric alcohol, and aliphatic hydroxycarboxylic acid.

The aliphatic unsaturated polybasic acid is generally preferably dibasic acid.

Examples of the aliphatic unsaturated polybasic acid include fumaric acid, maleic acid, maleic anhydride, itaconic acid, itaconic anhydride, citraconic acid and citraconic anhydride. The amount of the aliphatic unsaturated polybasic acid to be used is preferably from 0.1% by mol to 20% by mol, more preferably from 0.5% by mol to 10% by mol, still more preferably from 1% by mol to 5% by mol relative to the polybasic acid to be used.

Specific examples of the aliphatic saturated polybasic acid include oxalic acid, malonic acid, succinic acid, glutaric acid, adipic acid, pimelic acid, suberic acid, azelaic acid, sebacic acid and butanetetracarboxylic acid.

The polyhydric alcohol is generally preferably bifunctional alcohol.

Specific examples of the polyhydric alcohol include bifunctional alcohols such as ethylene glycol, diethylene glycol, triethylene glycol, polyethylene glycol, propylene glycol, dipropylene glycol, 1,3-butanediol, 1,4-butanediol, 3-methyl-1,5-pentanediol, 1,6-hexanediol, 1,9-nonanediol, neopentyl glycol and polytetraethylene glycol.

Examples also include tri- or higher functional alcohols such as glycerin and trimethylol propane. Such alcohols may also be included in a small amount.

In particular, a polymer of ethylene glycol, represented by Formula (1) below, is preferable, and diethylene glycol and triethylene glycol are particularly preferable:

$$HO\text{—}(\text{—}CH_2CH_2O\text{—})_n\text{—}H \qquad (1)$$

wherein n satisfies $2 \leq n \leq 10$.

Specific examples of the hydroxycarboxylic acid include glycolic acid, lactic acid, 6-hydroxycaproic acid, or any combination thereof. A combination of lactic acid and 6-hydroxycaproic acid is particularly preferable. The compositional ratio of such a combination is as follows: preferably, from 30% by mol to 70% by mol of lactic acid and from 70% by mol to 30% by mol of 6-hydroxycaproic acid, more preferably from 50% by mol of lactic acid and 50% by mol of 6-hydroxycaproic acid.

Such a combination is preferably one having a melting point of 25° C. or less when the resulting polyester is a crystalline polymer, and is preferably one having a glass transition point of 25° C. or less when the resulting polyester is an amorphous polymer. Examples include a polyester of diethylene glycol and a mixture of succinic acid and fumaric acid, a polyester of triethylene glycol and a mixture of succinic acid and fumaric acid, a polyester of diethylene glycol and a mixture of adipic acid and fumaric acid, and a polyester of triethylene glycol and a mixture of adipic acid and fumaric acid. Examples include a polyester of lactic acid, 6-hydroxycaproic acid, and a mixture of itaconic acid and triethylene glycol, a polyester of lactic acid, 6-hydroxycaproic acid, and a mixture of itaconic acid and diethylene glycol, and a polyester of lactic acid, 6-hydroxycaproic acid, and a mixture of fumaric acid and diethylene glycol.

The aliphatic polyester to be crosslinked may be subjected to chain extension with a binder like a diisocyanate compound, and may have a urethane bond in the structure thereof.

Specific examples of the method of crosslinking the aliphatic polyester can include thermal polymerization by heat, photopolymerization by ultraviolet light, and polymerization by γ-ray.

In general, photopolymerization by ultraviolet light can be suitably adopted in terms of the scale of a required apparatus, and the like, because photopolymerization enables curing to be made for from several seconds to several minutes, while thermal polymerization causes several hours to several-ten hours to be taken for crosslinking.

A radical generator in thermal polymerization, namely, a radical polymerization initiator is not particularly limited, and known peroxides such as benzoyl peroxide, p-chlorobenzoyl peroxide, lauroyl peroxide, acetyl peroxide, di-t-butyl peroxide, 1,1-bis(t-butylperoxy)-3,3,5-trimethylcyclohexane, t-butylperoxy pivalate, t-butylperoxy-2-ethylhexanoate, t-butylperoxy benzoate, bis(4-t-butylcyclohexyl)peroxy dicarbonate, diisopropylperoxy dicarbonate and t-butylperoxyisopropyl carbonate, and known azo compounds such as azobisisobutyronitrile are used. These may be used singly or in mixture of two or more kinds thereof.

Such a radical initiator is used in a proportion of from 0.005 parts by mass to 5 parts by mass, preferably from 0.01 parts by mass to 3 parts by mass with respect to 100 parts by mass of the aliphatic polyester including aliphatic unsaturated polybasic acid, and is preferably used at a mole equal to or more than the mole of the polymerization inhibitor included in the aliphatic polyester. When curing is conducted by a thermal polymerization method, the polymerization temperature and the polymerization time are selected, if appropriate depending on the radical polymerization initiator to be used, the size of a cured product, and the like.

The radical generator in photopolymerization by ultraviolet light, namely, a sensitizer is not particularly limited, and known 4-phenoxydichloroacetophenone, 4-t-butyl-dichloro-acetophenone, 4-t-butyl-trichloroacetophenone, and the like are used. These may be used singly or in mixture of two or more kinds thereof.

The sensitizer is used in a proportion of from 0.005 parts by mass to 5 parts by mass, preferably from 0.01 parts by mass to 3 parts by mass with respect to 100 parts by mass of the aliphatic polyester including aliphatic unsaturated polybasic acid. The radical polymerization initiator can also be used in combination with the sensitizer. No radical polymerization initiator is particularly required in polymerization by γ-ray.

The layer (A) may include any component other than such at least one elastomer selected from the group consisting of an acrylic thermoplastic elastomer and a polyester-based thermoplastic elastomer. Examples of such any other component include a softener. Examples of the softener include a conventionally known softener, and the softener, to be, if necessary, compounded to the composition (X) may be adopted. Examples of such any other component include other additives described above, to be, if necessary, compounded to the composition (X).

The layer (B) is a layer layered on the layer (A), and is a layer positioned opposite to the row of teeth when viewed from the layer (A) in wearing of the mouthpiece on the row of teeth. The adhesion strength between the layer (A) and the layer (B) is 30 MPa or more, preferably 50 MPa or more.

The difference between the bending elastic modulus of the layer (A) and the bending elastic modulus of the layer (B) (namely, absolute value of the difference; much the same is true on the following.) is preferably from 1500 MPa to 3000 MPa.

The layer (B) contains at least one polymer selected from the group consisting of poly(meth)acrylate and polyester.

The poly(meth)acrylate which can be used is a common poly(meth)acrylate including a structural unit derived from (meth)acrylate (hereinafter, also referred to as "(meth)acrylate unit").

The poly(meth)acrylate may be a homopolymer of acrylate, may be a homopolymer of methacrylate, or may be a copolymer of acrylate and methacrylate.

The content of the (meth)acrylate unit in the poly(meth)acrylate with respect to the total amount of the poly(meth)acrylate is preferably from 50% by mass to 100% by mass, more preferably from 60% by mass to 100% by mass, particularly preferably from 80% by mass to 100% by mass.

The poly(meth)acrylate is preferably any poly(meth)acrylate other than the acrylic thermoplastic elastomer which can be included in the layer (A).

The poly(meth)acrylate preferably includes a methacrylate unit.

The content of the methacrylate unit in the poly(meth)acrylate with respect to the total amount of the poly(meth)acrylate is preferably from 50% by mass to 100% by mass, more preferably from 60% by mass to 100% by mass, particularly preferably from 80% by mass to 100% by mass.

The (meth)acrylate unit is preferably an alkyl (meth)acrylate unit.

The number of carbon atom(s) in the alkyl portion of the alkyl (meth)acrylate unit is preferably from 1 to 6, more preferably from 1 to 3, still more preferably 1 or 2, particularly preferably 1 (namely, the alkyl (meth)acrylate unit is a methyl (meth)acrylate unit).

The poly(meth)acrylate may include a structural unit other than the (meth)acrylate unit.

Examples of the structural unit other than the (meth)acrylate unit include a structural unit derived from (meth)acrylic acid (preferably methacrylic acid) and a structural unit derived from α-olefin (preferably, ethylene, propylene or butylene).

The poly(meth)acrylate is preferably a polymethyl methacrylate (PMMA) or methyl methacrylate-methacrylic acid copolymer (MMA-MAA copolymer), particularly preferably PMMA.

The polyester which can be used is a common polyester which is a polycondensate of at least one polyvalent carboxylic acid and at least one polyalcohol.

The polyvalent carboxylic acid is preferably dicarboxylic acid, and terephthalic acid or 2,6-naphthalenedicarboxylic acid is more preferable.

The polyalcohol is preferably glycol (namely, diol), and ethylene glycol, 1,3-cyclobutanediol, 1,4-cyclohexanedimethanol or 2,2,4,4-tetramethyl-1,3-cyclobutanediol is more preferable.

When one kind of polyalcohol is used, such one kind of polyalcohol is preferably ethylene glycol, when two or more kinds of polyalcohols are used, one of two or more kinds of polyalcohols is preferably ethylene glycol, and, still more preferably, one of two or more kinds of polyalcohols is ethylene glycol and another thereof is 1,4-cyclohexanedimethanol.

The polyester is preferably polyethylene terephthalate (PET), glycol-modified polyethylene terephthalate (PETG) or polyethylene naphthalate (PET).

Any known polyester described in WO 2013/061462, JP-A No. 2009-513800, JP-A No. 2009-513801, and the like can also be used.

Examples of preferable polyester also include a polycondensate X of terephthalic acid, and 2,2,4,4-tetramethyl-1,3-cyclobutanediol and 1,4-cyclohexanedimethanol (CHDM).

The proportion of the terephthalic acid residue in the polycondensate X is preferably from 30% by mol to 70% by mol, more preferably from 40% by mol to 60% by mol.

The proportion of the 2,2,4,4-tetramethyl-1,3-cyclobutanediol residue in the polycondensate X is preferably from 5% by mol to 25% by mol, more preferably from 10% by mol to 20% by mol.

The proportion of the 1,4-cyclohexanedimethanol residue in the polycondensate X is preferably from 25% by mol to 50% by mol, more preferably from 30% by mol to 40% by mol.

The glass transition temperature (Tg) of the polycondensate X is preferably from 99° C. to 125° C.

The mass average molecular weight (Mw) of each of the poly(meth)acrylate and the polyester is preferably from 10000 to 1000000, more preferably from 20000 to 800000, particularly preferably from 50000 to 500000.

When the layer (B) contains poly(meth)acrylate or polyester, the content of the poly(meth)acrylate or polyester with respect to the total amount of the layer (B) is preferably from 50% by mass to 100% by mass, more preferably from 60% by mass to 100% by mass, particularly preferably from 80% by mass to 100% by mass.

The layer (B) may include any component other than such at least one polymer selected from the group consisting of poly(meth)acrylate and polyester.

Examples of such other component which can be contained in the layer (B) include the same components as other components which can be contained in the layer (A).

Hereinafter, one example of the mouthpiece is described with reference to FIG. 12 and FIG. 13.

Figure 12:
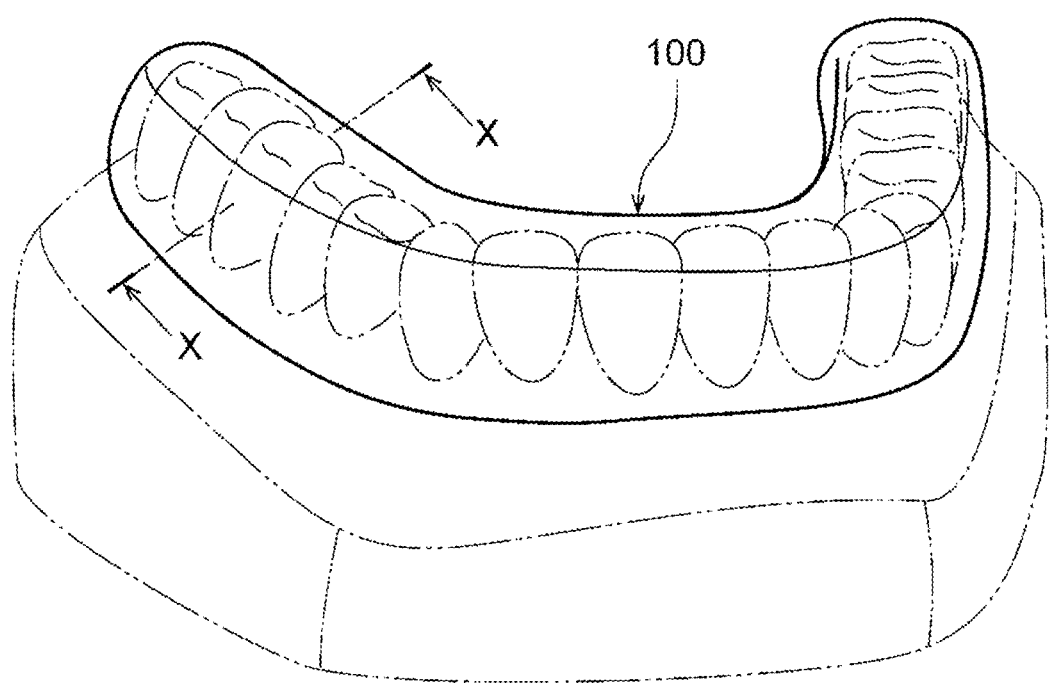
FIG. 12 includes a perspective view illustrating a schematic configuration of a mouthpiece according to one example of the third aspect.
Figure 13:
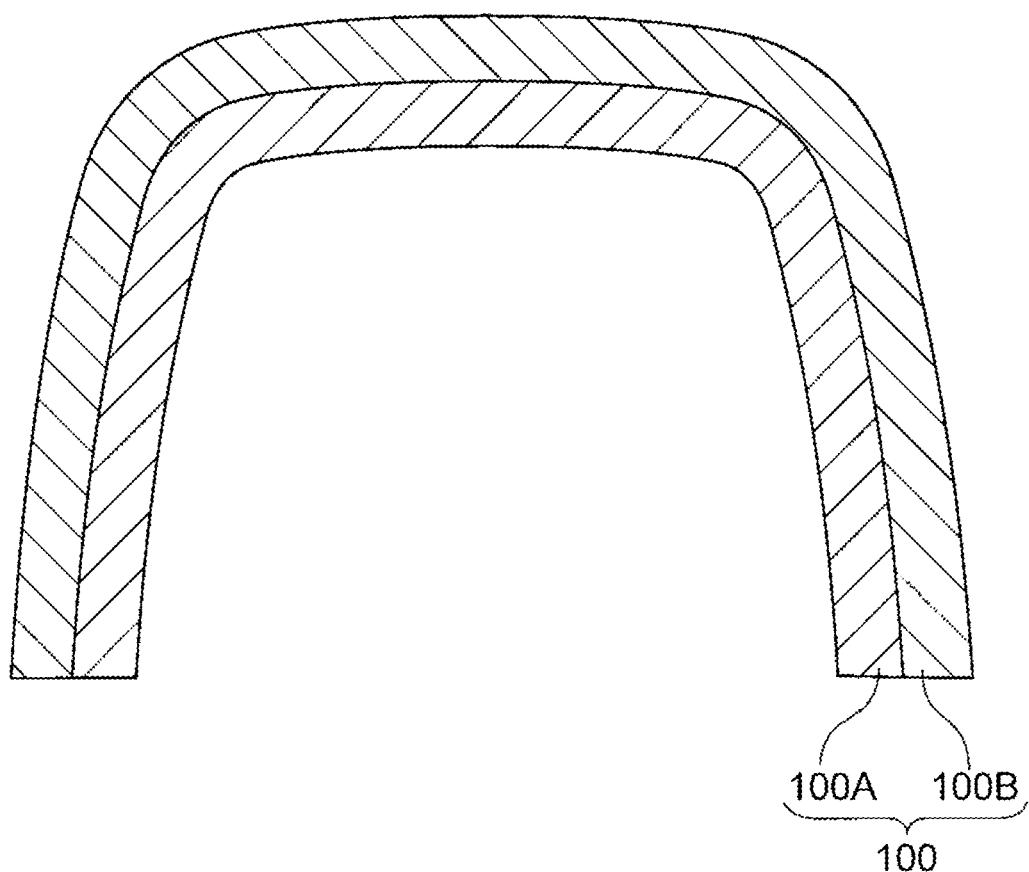
FIG. 13 includes an X-X line cross-sectional view of FIG. 12.

As illustrated in FIG. 12 and FIG. 13, a mouthpiece 100 has a layered structure including a layer (A) 100A positioned closer to the row of teeth in wearing and a layer (B) 100B layered on the layer (A) and positioned opposite to the row of teeth in wearing when viewed from the layer (A).

The mouthpiece 100 is one mandible mouthpiece example.

In the mouthpiece 100, the layer (A) 100A contains at least one elastomer selected from the group consisting of an acrylic thermoplastic elastomer and a polyester-based thermoplastic elastomer, the layer (B) 100B contains at least one polymer selected from the group consisting of poly(meth)acrylate and polyester, the adhesion strength between the layer (A) 100A and the layer (B) 100B is 30 MPa or more, the bending elastic modulus of the layer (A) 100A is from 50 MPa to 300 MPa, the bending elastic modulus of the layer (B) 100B is higher than the bending elastic modulus of the layer (A) 100A, and the difference between the bending elastic modulus of the layer (A) 100A and the bending elastic modulus of the layer (B) 100B is from 1000 MPa to 3000 MPa.

In such one example, at least one of a maxillary piece 1 or a mandible piece 2 includes a layered structure (not illustrated) including the layer (A) and layer (B).

[Production Method of Mouthpiece]

The method of producing a mouthpiece, of the aspect, is not particularly limited, and a known method can be adopted, if appropriate. Examples of a preferable production method of a mouthpiece include from first to third production methods.

<First Production Method>

The first production method is a production method of a mouthpiece to be worn on the row of teeth, in which the mouthpiece has a layered structure including a layer (A) closer to the row of teeth in wearing of the mouthpiece on the row of teeth and a layer (B) layered on the layer (A) and disposed opposite to the row of teeth in the wearing when viewed from the layer (A), the layer (A) contains at least one elastomer selected from the group consisting of an acrylic thermoplastic elastomer and a polyester-based thermoplastic elastomer, and the layer (B) contains poly(meth)acrylate, the method including:

a step of hot forming an elastomer sheet containing the at least one elastomer, to thereby form the layer (A), and a step of building up a precursor of poly(meth)acrylate on the surface opposite to the layer (A) (namely, the surface opposite to the row of teeth in wearing when viewed from the layer (A)), and then curing the resultant, to thereby form the layer (B) containing poly(meth)acrylate.

The bending elastic modulus of the elastomer sheet before hot forming is preferably from 50 MPa to 300 MPa. A preferable range of the bending elastic modulus of the elastomer sheet before hot forming is the same as a preferable range of the bending elastic modulus of the layer (A).

The elastomer sheet before hot forming can be produced by a known method such as press molding or extrusion molding.

The hot forming for forming the elastomer sheet into the layer (A) is preferably performed by using a model for mouthpiece formation (mandible model or maxillary model). It is here more preferable that the sheet is softened and the sheet softened is molded into a mouthpiece shape adapted to the shape of the model. The hot forming which can be applied is suction molding, pressure molding, suction and pressure molding, or the like.

Examples of the precursor of poly(meth)acrylate include (meth)acrylate (monomer), an oligomer of (meth)acrylate, a prepolymer of (meth)acrylate, (meth)acrylic acid (monomer), an oligomer of (meth)acrylic acid, a prepolymer of (meth)acrylic acid, or a mixture thereof. Methacrylate (monomer), an oligomer of methacrylate, a prepolymer of methacrylate, methacrylic acid (monomer), an oligomer of methacrylic acid, a prepolymer of methacrylic acid, or a mixture thereof is preferable.

The building up of the precursor of poly(meth)acrylate on the layer (A) can be performed according to a procedure known in the dental material field.

The curing of the precursor of poly(meth)acrylate built up on the layer (A) can also be performed according to a method known in the dental material field, such as photopolymerization or thermal polymerization.

In the first production method, the bending elastic modulus of the elastomer sheet before hot forming is preferably from 50 MPa to 300 MPa. A preferable range of the bending elastic modulus of the elastomer sheet before hot forming is the same as a preferable range of the bending elastic modulus of the layer (A).

In a case in which the precursor of poly(meth)acrylate is cured in the same conditions as the curing conditions for providing the layer (B), to thereby provide a sheet B, it is preferable that the bending elastic modulus of the sheet B is higher than the bending elastic modulus of the elastomer sheet before hot forming, and the difference between the bending elastic modulus of the elastomer sheet before hot forming and the bending elastic modulus of the sheet B is from 1000 MPa to 3000 MPa.

A preferable range of the difference between the bending elastic modulus of the elastomer sheet before hot forming and the bending elastic modulus of the sheet B is the same as a preferable range of the difference between the bending elastic modulus of the layer (A) and the bending elastic modulus of the layer (B).

<Second Production Method>

The second production method is a production method of a mouthpiece to be worn on the row of teeth, in which the mouthpiece has a layered structure including a layer (A) closer to the row of teeth in wearing of the mouthpiece on the row of teeth and a layer (B) layered on the layer (A) and disposed opposite to the row of teeth in the wearing when viewed from the layer (A), the layer (A) contains at least one elastomer selected from the group consisting of an acrylic thermoplastic elastomer and a polyester-based thermoplastic elastomer, and the layer (B) contains polyester, the method including a step of hot forming a layered sheet including an elastomer sheet containing the at least one elastomer and a polyester sheet layered on the elastomer sheet, containing polyester, to thereby provide a mouthpiece having the layered structure.

The layered sheet can be produced in the step of providing a mouthpiece, according to a known method such as heat-sealing, co-extrusion or extrusion coating of each sheet.

The hot forming of the layered sheet in the step of providing a mouthpiece is preferably performed using a model for mouthpiece formation (mandible model or maxillary model).

In the second production method, the bending elastic modulus of the elastomer sheet before layering is from 50 MPa to 300 MPa. A preferable range of the bending elastic modulus of the elastomer sheet before layering is the same as a preferable range of the bending elastic modulus of the layer (A).

A precursor is preferable which allows the bending elastic modulus of the polyester sheet before layering to be higher than the bending elastic modulus of the elastomer sheet before layering and which allows the difference between the bending elastic modulus of the elastomer sheet before layering and the bending elastic modulus of the polyester sheet before layering to be from 1000 MPa to 3000 MPa.

<Third Production Method>

The third production method is a production method of a mouthpiece to be worn on the row of teeth, in which the mouthpiece has a layered structure including a layer (A) closer to the row of teeth in wearing of the mouthpiece on the row of teeth and a layer (B) layered on the layer (A) and disposed opposite to the row of teeth in the wearing when viewed from the layer (A), the layer (A) contains at least one elastomer selected from the group consisting of an acrylic thermoplastic elastomer and a polyester-based thermoplastic elastomer, and the layer (B) contains at least one polymer selected from the group consisting of poly(meth)acrylate and polyester, the method including a step of hot forming an elastomer sheet containing the at least one elastomer to thereby form the layer (A), and a step of heat-sealing a sheet containing at least one polymer (hereinafter, also referred to as "polymer-containing sheet") onto the surface opposite to the layer (A) (namely, the surface opposite to the row of teeth in wearing, when viewed from the layer (A)), to thereby form the layer (B) containing the at least one polymer.

The heat-sealing of the polymer-containing sheet onto the layer (A) can be performed by the same procedure as in the hot forming of the elastomer sheet into the shape of the layer (A), except that a model for mouthpiece formation (mandible model or maxillary model), to which the layer (A) is worn, is used.

The bending elastic modulus of the elastomer sheet before hot forming is from 50 MPa to 300 MPa in the third production method. A preferable range of the bending elastic modulus of the elastomer sheet before hot forming is the same as a preferable range of the bending elastic modulus of the layer (A).

A precursor is preferable which allows the bending elastic modulus of the polymer-containing sheet before heat-sealing to be higher than the bending elastic modulus of the elastomer sheet before hot forming and which allows the difference between the bending elastic modulus of the elastomer sheet before hot forming and the bending elastic modulus of the polymer-containing sheet before heat-sealing to be from 1000 MPa to 3000 MPa.

<Fourth Aspect>

[Mouthpiece]

Hereinafter, one embodiment of the mouthpiece of the fourth aspect is described.

The mouthpiece according to the present aspect includes a constituent portion (X) which includes an olefin-based polymer (A) having a repeating unit having 2 or 3 carbon atoms (hereinafter, also referred to as "olefin polymer (A)") and which satisfies a Shore A hardness of more than 80 and less than 86.

A portion corresponding to the constituent portion (X) in the mouthpiece according to the aspect is not particularly limited, and is, for example, the same as in the second aspect.

The constituent portion (X) includes the olefin polymer (A), thereby suppressing breeding of bacteria and also exhibiting proper flexibility and hardness, as compared with the case of formation by EVA. Therefore, the mouthpiece according to the embodiment can be easily processed by polishing a section corresponding to the constituent portion (X), and thus can be modified into a shape adapted to the row of teeth and the like of a wearer by polishing a portion corresponding to the constituent portion (X) when the size and the shape of the mouthpiece is not adapted to the row of teeth of the wearer.

A commercially available product may be used as the olefin polymer (A), and examples include TAFMER DF-810 (Mitsui Chemicals, Inc.). Vistamaxx 6102 (produced by Exxon Mobil Corporation) and Zeras (produced by Mitsubishi Chemical Corporation).

The constituent portion (X) may have the same physical properties and include the same components as those of the constituent portion (X) in the second aspect.

The mouthpiece may satisfy the following conditions (a) to (c). Thus, the impact resilience rate ($\gamma$) of the constituent portion (X), described below, can be a predetermined value:

(a) the olefin-based polymer (A) includes from 51 parts by mass to 90 parts by mass of an olefin-based polymer component (A-1) (also referred to as "component (A-1)") having a melting point of from 100° C. to 170° C. measured according to a DSC (differential scanning calorimetry) method, with respect to 100 parts by mass of the olefin-based polymer (A);

(b) the olefin-based polymer (A) includes from 10 parts by mass to 49 parts by mass of an olefin-based polymer component (A-2) (also referred to as "component (A-2)") having a melting point of 95° C. or less or having substantially absent melting point, measured according to a DSC method, with respect to 100 parts by mass of the olefin-based polymer (A); and (c) the olefin-based polymer (A) has a bending elastic modulus ($\alpha$) at 23° C., of 5 MPa$\leq\alpha\leq$100 MPa.

The component (A-1) is not particularly limited as long as the component has a repeating unit having 2 or 3 carbon atoms and has a melting point of from 100° C. to 170° C., as measured by a DSC method, and for example, an olefin-based polymer including from 90% by mol to 100% by mol of a repeating unit derived from propylene is preferable and an olefin-based polymer including from 95% by mol to 100% by mol is more preferable.

The component (A-1) may include at least one of a repeating unit derived from ethylene or a repeating unit derived from the above-described other monomer, other than the repeating unit derived from propylene.

The melting heat quantity ($\Delta H_C$) of the component (A-1), as measured by a DSC method, is preferably 20 J/g or more, more preferably 40 J/g or more, still more preferably 50 J/g or more. The upper limit of the melting heat quantity ($\Delta H_C$) is not particularly limited, and the melting heat quantity ($\Delta H_C$) may be, for example, 120 J/g or less.

The melting point of the component (A-1), as measured by a DSC method, is preferably 120° C. or more, more preferably 140° C. or more, still more preferably 150° C. or more from the viewpoints of moldability, heat resistance and mechanical properties.

The limiting viscosity [$\eta$] of the component (A-1), as measured in decalin at 135° C., is preferably from 0.5 dL/g to 10 dL/g, more preferably from 1.0 dL/g to 6.0 dL/g, still more preferably from 1.0 dL/g to 4.0 dL/g. Thus, the component (A-1) exhibits favorable fluidity and allows for easy compounding with other component, and a mouthpiece which is excellent in mechanical strength tends to be obtained.

The melt flow rate (MFR) of the component (A-1), as measured at 230° C. and at a load of 2.16 kg according to ASTM D 1238, is preferably from 0.001 g/10 minutes to 50 g/10 minutes, more preferably from 0.1 g/10 minutes to 30 g/10 minutes, still more preferably from 0.1 g/10 minutes to 10 g/10 minutes.

The component (A-2) is not particularly limited as long as the component has a repeating unit having 2 or 3 carbon atoms and has a melting point of from 95° C. or less or substantially no melting point, as measured by a DSC method, and for example, an olefin-based polymer including 40% by mol or more and less than 90% by mol of a repeating unit derived from propylene is preferable and an olefin-based polymer including from 50% by mol to 85% by mol of a repeating unit derived from propylene is more preferable.

The component (A-2) may include at least one of a repeating unit derived from ethylene or a repeating unit derived from the above-described other monomer, other than the repeating unit derived from propylene.

The melting heat quantity ($\Delta H_C$) of component (A-2), as measured by a DSC method, is preferably 10 J/g or less, more preferably 5 J/g or less, still more preferably 1 J/g or less.

The melting point of component (A-2), as measured by a DSC method, is preferably 90° C. or less or substantially absent, more preferably 80° C. or less or substantially absent.

The phrase "melting point being substantially absent" means that the melting heat quantity $\Delta H_c$ due to a melting peak is 1 J/g or less.

The limiting viscosity [$\eta$] of the component (A-2), as measured in decalin at 135° C., is preferably from 0.01 dL/g to 10 dL/g, more preferably from 0.05 dL/g to 10 dL/g, still more preferably from 0.1 dL/g to 5.0 dL/g. When the limiting viscosity ranges from 0.01 dL/g to 10 dL/g, the component (A-2) exhibits favorable fluidity and allows for easy compounding with other component, and a mouthpiece which is excellent in mechanical strength tends to be obtained.

The melt flow rate (MFR) of the component (A-2), as measured at 230° C. and at a load of 2.16 kg according to ASTM D 1238, is preferably from 0.01 g/10 minutes to 100 g/10 minutes, more preferably from 0.01 g/10 minutes to 50 g/10 minutes, still more preferably from 0.1 g/10 minutes to 30 g/10 minutes, particularly preferably from 0.1 g/10 minutes to 10 g/10 minutes.

The bending elastic modulus ($\alpha$) at 23° C. of the olefin-based polymer (A) is preferably 5 MPa$\leq\alpha\leq$100 MPa, more preferably 10 MPa$\leq\alpha\leq$95 MPa, still more preferably 30 MPa$\leq\alpha\leq$90 MPa, particularly preferably 35 MPa$\leq\alpha\leq$85 MPa, from the viewpoints of wearing property and polishing workability.

The impact resilience rate ($\gamma$) of the constituent portion (X) is preferably 0%$\leq\gamma\leq$25%, more preferably 1%$\leq\gamma\leq$20%. The impact resilience rate ($\gamma$) of the constituent portion (X) is 25% or less, thereby relaxing an impact on the teeth to result in an enhancement in comfort in the oral cavity.

The mouthpiece may include a layered structure having another layer, together with a layer (LI) corresponding to the constituent portion (X) of the aspect (hereinafter, also referred to as "LI layer"). For example, the mouthpiece may include not only the LI layer, but also the LO layer in the second aspect.

The LI layer in the fourth aspect may satisfy any of the physical conditions of the LI layer in the second aspect.

It is preferable that a layered sheet formed from the olefin-based polymer (A) forming the LI layer and the olefin-based polymer forming the LO layer satisfies a bending elastic modulus ($\alpha$) at 23° C., of 80 MPa$\leq\alpha\leq$1000 MPa.

[Sheet for Production of Mouthpiece Piece Unit]

The sheet for production of a mouthpiece piece unit, according to the present aspect, is a sheet for forming the constituent portion (X). The sheet for production of a mouthpiece piece unit, according to the aspect, has proper flexibility and hardness, and therefore is excellent in moldability, and can produce a mouthpiece excellent in polishing workability.

[Production Method of Mouthpiece]

The mouthpiece according to the aspect can be obtained by hot forming the sheet for production of a mouthpiece piece unit, of the fourth aspect.

The mouthpiece according to the aspect can be produced by the same method as that of a conventional mouthpiece except that the sheet for producing a piece unit, having the above-described material, physical properties and structure, is used as the material, and can be produced by the method described in the second aspect.

EXAMPLES

Hereinafter, the invention is described with reference to Examples, but the invention is not intended to be limited to these Examples at all. Each value of physical properties was measured as follows in each Example.

<Water Absorption Rate (Table 1 to Table 5)>

The monolayer sheet, the layered sheet, the sheet used in layer (A) formation or the PMMA sheet used in monolayer mouthpiece formation, obtained in each Example, was immersed in a water bath at 37° C. for 24 hours and the water absorption rate (%) after immersion was determined, according to ASTM D570-98:2010.

<Coffee Staining Property (Table 1, Table 2 and Table 5)>

The monolayer sheet or the layered sheet, obtained in each Example, was immersed in a coffee liquid in which a commercially available instant coffee was adjusted to in 1.4% by mass, and kept at 37° C. for 24 hours. The sheet taken out after 24 hours was evaluated about coloration thereof by color difference ($\Delta E$) measurement with Colour Cute i Model CC-i (manufactured by Suga Test Instruments Co., Ltd.) by use of a reflection mode.

<Polishing Workability (Table 1, Table 2 and Table 5)>

Evaluation of polishing workability of the mouthpiece was performed as follows.

Polishing was conducted at a bar rotation speed of ULTIMATE XL (manufactured by NSK) of 15000 rpm using CX251G (manufactured by Diaswiss S.A.) for metal polishing, at a depth of 1 cm for about 30 seconds. A case in which fluffing was visually observed was rated as "Grade 5". Polishing was then conducted by use of SA Point (manufactured by Akiyama Sangyo Co. Ltd.) for sponge polishing, and a case in which fluffing was visually observed was rated as "Grade 4". Polishing was then conducted by use of Lisko S (manufactured by ERKODENT) for fine polishing, and a case in which fluffing was visually observed was rated as "Grade 3" and a case in which no fluffing was observed was rated as "Grade 2". A case in which the mouthpiece was flexible and was difficult to stably polish was rated as "Grade 1".

<Wear Feeling (Table 1 and Table 2)>

The mouthpiece was worn on the teeth for 15 minutes, and wear feeling of the mouthpiece was evaluated according to the following Grades. A case in which wearing could be made without any feeling of strangeness in wearing and no pain was caused on the row face of teeth in wearing at all was rated as "Grade 5". A case in which any feeling of strangeness was slightly caused in wearing, but was not problematic in terms of practical use and no pain was caused on the row face of teeth in wearing at all was rated as "Grade 4". A case in which any feeling of strangeness was slightly caused in wearing, but was not problematic in terms of practical use and no feeling of strangeness was caused in wearing at all was rated as "Grade 3". A case in which any feeling of strangeness was caused in wearing and any pain was caused on the row face of teeth in wearing was rated as "Grade 2". A case in which any feeling of strangeness was remarkably caused in wearing and any pain was remarkably caused on the row face of teeth in wearing was rated as "Grade 1".

<Wear Feeling (Table 3 and Table 4)>

The mouthpiece was worn on the teeth for 15 minutes, and a case in which wearing could be made without any feeling of strangeness in wearing and no pain was caused on the row face of teeth in wearing was rated as "Grade 3". A case in which there was at least one of any feeling of strangeness caused in wearing or any pain caused on the row face of teeth in wearing was rated as "Grade 2". A case in which adhesion between the layer (A) and the layer (B) was not almost obtained and there was a difficulty in wearing as a layered mouthpiece was rated as "Grade 1".

<Bending Elastic Modulus (Table 1 to Table 5)>

The bending elastic modulus ($\alpha$) of the monolayer sheet, the layered sheet, the sheet used in layer (A) formation or the PMMA sheet used in monolayer mouthpiece formation was measured in conditions of an atmosphere at 23° C. and a speed of 1 mm/min according to JIS K7171:2008, and the resulting value was defined as the bending elastic modulus.

<Bending Elastic Modulus (Table 3 and Table 4)>

A sheet having a thickness of 1 mm was produced using "Orthocryl" used in layer (B) formation in the same conditions as those of layer (B) production conditions (the volume ratio of the powder and the liquid, polymerization conditions and the like). The bending elastic modulus of the resulting sheet, the sheet used in layer (B) formation or PMMA sheet used in monolayer mouthpiece formation was measured in conditions of an atmosphere at 23° C. and a speed of 1 mm/min according to JIS K7171:2008, and the resulting value was defined as the bending elastic modulus ($\beta$).

<Difference ($\beta-\alpha$) in Bending Elastic Modulus between Layer (A) and Layer (B), Table 3 and Table 4>

The difference ($\beta-\alpha$) in the bending elastic modulus between the layer (A) and the layer (B) was calculated by subtracting the bending elastic modulus ($\alpha$) from the bending elastic modulus ($\beta$).

<Shore A Hardness, Table 3 to Table 5)>

The Shore A hardness (durometer hardness, Type A) of the sheet used in layer (A) formation, the PMMA sheet used in monolayer mouthpiece formation, or the monolayer sheet obtained in each Example was measured according to JIS K6253-3:2012, and the resulting value was defined as the Shore A hardness of the layer (A).

<Adhesion Strength between Layer (A) and Layer (B) (Table 3 and Table 4)>

Examples 1B and 2B, and Comparative Examples 1B and 2B

A flat plate (A) of 7 cm in length×2 cm in width was cut out from the sheet used in layer (A) formation.

A sheet having a thickness of 1 mm was produced using "Orthocryl" used in layer (B) formation in the same conditions as those of layer (B) production conditions (the volume ratio of the powder and the liquid, polymerization conditions and the like), and a flat plate (B) of 7 cm in length×2 cm in width was cut out from the resulting sheet.

A region of 1 cm in length×2 cm in width of the flat plate (A) was coated with an adhesion resin (DP-8010 Blue produced by 3M) at a thickness of 0.1 mm, and the flat plate (A) and the flat plate (B) were then bonded with the adhesion resin interposed. After a lapse of 24 hours of bonding, the flat plate (B) was pulled using ZTS-1000 manufactured by IMADA CO., LTD, in the direction perpendicular to the flat plate (A) until breakage, and the breakage point was defined as the adhesion strength between the layer (A) and the layer (B).

Examples 3B to 9B, and Comparative Examples 3B and 4B

The adhesion strength between the layer (A) and the layer (B) was measured in the same manner as in Example 1B except that the flat plate (B) was changed to a flat plate (B) of 7 cm in length×2 cm in width, cut out from the sheet used in layer (B) formation.

<Impact Resilience Rate (Table 5)>

The rebound height L (mm) in dropping of 16.310 g of a hard sphere from a height of 460 mm onto the monolayer sheet obtained in each Example was measured according to JIS K6400, and the impact resilience rate defined according to the following Formula was determined to evaluate impact absorption.

Impact Resilience Rate (%)=[$L$(mm)/460]×100

<Bacterial Adhesion Property (Table 5)>

A test piece obtained by cutting out the monolayer sheet obtained in each Example to 1 cm in square was placed in a 12-well cell culture plate, and two positions of the plate were secured by use of a composite resin for dental filling, Fantasista (produced by Sun Medical Co., Ltd.). 50 μL of a suspension (turbidity $OD_{600}$ at 600 nm=0.7, by a spectrophotometer (WPA, C08000 Cell Density Meter)) prepared by culturing *Streptococcus mutans* (NBRC 13955, furnished from National Institute of Technology and Evaluation, Biotechnology center) in a BHI (brain heart infusion) culture medium was dropped on the test piece, and cultured under an anaerobic condition at 37° C. for two hours. Next, 3 mL of a BHI culture medium including 5% by mass of sucrose was dropped on the surface of the test piece. Culturing was again conducted under an anaerobic condition at 37° C. for six hours.

The test piece was taken out from the culture medium into a dish having a diameter of 35 mm, and bacteria not adhering to the test piece were washed off by PBS (phosphate buffered saline). The test piece was transferred to a centrifuge tube, and 3 mL of an aqueous 1.0 N sodium hydroxide solution was added thereto. The centrifuge tube was shaken to peel off a biofilm on the test piece, and thereafter the biofilm was immersed in a warm bath at 37° C. for one hour. Centrifugation (2000×g, one minute) was then conducted, the supernatant liquid was subjected to quantitative determination by a phenol-sulfuric acid analysis method, and the absorbance at 490 nm was measured by a microplate reader to quantitatively determine the amount of sugar. The results are shown in Table 5. The numerical values described in Table 5 means that the amount of adhesion of the biofilm is larger and the bacterial adhesion property is higher as the amount of sugar is larger.

<Sheet Moldability (Table 5)>

The monolayer sheets obtained in respective Examples were used for mouthpiece molding, and the sheet moldability was evaluated. A monolayer sheet which could be molded into a mouthpiece along with the row face of teeth was rated as "3", a monolayer sheet which could be molded into a mouthpiece, but caused the thickness variation due to air bubbles and the like was rated as "2", and a monolayer sheet which could not be molded into any mouthpiece due to hanging and the like of the sheet was rated as "1", among the monolayer sheets obtained in respective Examples.

The sheet (monolayer sheet) for use in each of the following Examples 1A to 4A and Examples 101A to 104A was produced by subjecting each resin pellet to sheet molding at a pressure of 10 MPa by use of a hydraulic hot press machine manufactured by SHINTO Metal Industries Corporation, set to 190° C. In the case of a sheet having a thickness of from 0.5 to 2 mm (200×200×from 0.5 to 2 mm), a measurement sample was produced by pre-heating for about from five to seven minutes, application of a pressure of 10 MPa for from one to two minutes, thereafter compression at 10 MPa by use of another hydraulic hot press machine manufactured by SHINTO Metal Industries Corporation, set to 20° C., and cooling for about five minutes. A brass plate having a thickness of 5 mm was used as a hot plate.

In the case of use of a layered sheet for mouthpiece production, the layered sheet was produced by heat-sealing two monolayer sheets according to the above method.

Example 1A

A monolayer sheet having a thickness of 1 mm, made of soft olefin, was produced as sheet for an innermost layer (T1) by use of a commercially available olefin-based soft polymer TAFMER DF-810 (produced by Mitsui Chemicals. Inc.). The innermost layer (T1) corresponded to the L layer.

A monolayer sheet having a thickness of 1 mm of isotactic polypropylene (Prime Polypro [registered trademark] F327 (produced by Prime Polymer Co., Ltd.)) was produced as a sheet for an outermost layer (T2). The innermost layer (T2) corresponded to the LO layer.

An olefin-based layered sheet having a thickness of 2 mm was obtained by heat-sealing the sheet for an innermost layer (T1) and the sheet for an outermost layer (T2) being stacked.

An objective mouthpiece was obtained by subjecting the olefin-based layered sheet to suction molding at a stage where the sheet was softened and hung by 1.5 cm, by use of a mandible of INVICTUS manufactured by Nissin Dental Products INC., as a mouthpiece production model, and Modelcapture Try manufactured by SHOFU INC., as a mouthpiece-molding machine.

Examples 2A and 3A

Respective olefin-based layered sheets and respective mouthpieces were obtained in the same manner as in Example 1A except that TAFMER DF-810 used in production of the sheet for an innermost layer (T) was changed to NOTIO SN-0285 (produced by Mitsui Chemicals, Inc.) and Vistamaxx 6102 (produced by Exxon Mobil Corporation), respectively.

Example 4A

An olefin-based layered sheet and a mouthpiece were obtained in the same manner as in Example 1A except that each of the sheets for an innermost layer (T) and an outermost layer (T2) was changed so as to have a thickness of 2 mm.

Examples 101A and 102A

Each olefin-based monolayer sheet having a thickness of 2 mm or having a thickness of 3 mm, of isotactic polypropylene (Prime Polypro [registered trademark] F327 (produced by Prime Polymer Co., Ltd.)) was produced. Each objective mouthpiece was obtained in the same manner as in Example 1A.

Examples 103A and 104A

Each pellet was obtained by kneading isotactic polypropylene (Prime Polypro [registered trademark] F327 (produced by Prime Polymer Co., Ltd.)) and Exfola (registered trademark, produced by Mitsui Chemicals, Inc.), or 12P Mirason (produced by DU PONT-MITSUI POLYCHEMICALS) as polyethylene and Exfola (registered trademark, produced by Mitsui Chemicals, Inc.) as a polymer having a siloxane structure at a mass ratio of 9:1. Each objective mouthpiece was obtained in the same manner as in Example 101A except that the resulting pellet was used to produce an olefin-based monolayer sheet having a thickness of 3 mm.

Comparative Example 101A

A monolayer press sheet was produced in the same manner as in Example 101A except that Erkoflex (2 mm in thickness, manufactured by ERKODENT) which was a sheet of an ethylene-vinyl acetate copolymer was used, and respective physical properties thereof were evaluated. The coffee staining property was high and the polishing workability was also inferior.

Comparative Example 102A

A monolayer press sheet was produced in the same manner as in Example 101A except that Erkodul (2 mm in thickness, manufactured by ERKODENT) which was a PMMA sheet was used, and respective physical properties thereof were evaluated. A remarkable feeling of strangeness in wearing was caused and a remarkable pain to the row of teeth in wearing was caused in wear feeling evaluation. The water absorption property and the coffee staining property were high.

block copolymer of a hard block and a soft block, as a resin pellet of an acrylic elastomer (acrylic thermoplastic elastomer).

The hard block was a structural unit derived from methyl methacrylate, and had a glass transition temperature (Tg) of from 80° C. to 120° C. The soft block was a structural unit

TABLE 1

|  |  | Example 1A | Example 2A | Example 3A | Example 4A |
|---|---|---|---|---|---|
| Constituent portion (X) | Inner layer (T1) | TAFMER DF-810 | NOTIO SN-0285 | VISTAMAXX 6102 | TAFMER DF-810 |
|  | Outer layer (T2) | Polypropylene | Polypropylene | Polypropylene | Polypropylene |
| T1 layer thickness |  | 1 mm | 1 mm | 1 mm | 2 mm |
| T2 layer thickness |  | 1 mm | 1 mm | 1 mm | 2 mm |
| Bending elastic modulus α (MPa) |  | 155 | 160 | 102 | 93 |
| Bending elastic modulus α1 of T1 layer (MPa) |  | 35 | 47 | 8 | 35 |
| Bending elastic modulus α2 of T2 layer (Mpa) |  | 1062 | 1062 | 1062 | 1062 |
| Water absorption rate β (% by mass) |  | 0.02 | 0 | 0 | 0.6 |
| Coffee staining property γ (ΔE) |  | 0.29 | 0.1 | 0.97 | 0.18 |
| Polishing workability |  | 4 | 4 | 4 | 4 |
| Wear feeling |  | 4 | 4 | 4 | 4 |

TABLE 2

|  | Example 101A | Example 102A | Example 103A | Example 104A | Comparative Example 101A | Comparative Example 102A |
|---|---|---|---|---|---|---|
| Constituent portion (X) | Polypropylene | Polypropylene | 10% by mass of Exfola + polypropylene | 10% by mass of Exfola + polyethylene | Ethylene-vinyl acetate copolymer | PMMA |
| Thickness of constituent portion (X) | 2 mm | 3 mm | 3 mm | 3 mm | 2 mm | 2 mm |
| Bending elastic modulus α (MPa) | 821 | 638 | 724 | 337 | 29 | 2050 |
| Water absorption rate β (% by mass) | 0.16 | 0.02 | 0.08 | 0.06 | 0.14 | 1.45 |
| Coffee staining property (ΔE) | 0.25 | 0.3 | 0.27 | 0.31 | 9.1 | 2.17 |
| Polishing workability | 4 | 4 | 4 | 4 | 1 | 3 |
| Wear feeling | 3 | 3 | 3 | 3 | 3 | 1 |

Each sheet for use in the following Examples B1 to B9 was produced by subjecting each resin pellet to press molding at a pressure of 10 MPa by use of a hydraulic hot press machine manufactured by SHINTO Metal Industries Corporation, set to 190° C.

In the case of a sheet having a thickness of 2 mm (200 mm×200 mm×2 mm), the sheet was produced by preheating for about from about five minutes to seven minutes, application of a pressure of 10 MPa for from one minute to two minutes, thereafter compression at 10 MPa by use of another hydraulic hot press machine manufactured by SHINTO Metal Industries Corporation, set to 20° C., and cooling for about five minutes. A brass plate having a thickness of 5 mm was used as a hot plate.

Example 1B

An acrylic elastomer sheet having a thickness of 2 mm was produced using "KURARITY (registered trademark) LB550" produced by KURARAY CO., LTD., which was a derived from butyl acrylate, and had a glass transition temperature (Tg) of from −40° C. to −50° C.

A mouthpiece (layer (A)) was produced in the same manner as in Example 1A.

Next, a powder (polymethyl methacrylate and catalyst) of "Orthocryl" (precursor of PMMA) produced by Ortho Dentaurum and a liquid (methyl methacrylate) were kneaded at a volume ratio of 2.5:1, and the kneaded product obtained was built up on a surface of the mouthpiece (layer (A)), the surface being located opposite to the row of teeth in wearing.

Next, the mouthpiece (layer (A)) on which the kneaded product was built up was placed in a pressure cooker for polymerization, and the kneaded product was subjected to pressure polymerization in conditions of a pressure of 0.22 MPa, a water temperature of 40° C. and a polymerization time of 20 minutes, to thereby form a layer (B) made of PMMA The layer (B) was here formed so as to have a thickness of 1 mm. As described above, a layered mouthpiece (total thickness: 3 mm) was obtained.

Example 2B

A layered mouthpiece (total thickness: 3 mm) was obtained in the same manner as in Example 1B except that a surface of the layer (A), to which the kneaded product was to be built up, was roughly polished before the kneaded product was built up on the layer (A). Such rough polishing was performed using Carbide Bur for Dia-rub technique (manufactured by Diaswiss S.A.).

Example 3B

A mouthpiece (layer (A)) made of an acrylic elastomer was first obtained in the same manner as in Example 1B. Next, Erkocryl manufactured by ERKODENT (PMMA sheet; 1 mm in thickness) was heat-sealed to the layer (A) by suction molding at a stage of being softened and hung by 1.5 cm, by use of the mandible model where the mouthpiece (layer (A)) was formed and the molding machine (Modelcapture Try). As described above, a layered mouthpiece (total thickness: 3 mm) was obtained.

Example 4B

A layered mouthpiece (total thickness: 3 mm) was obtained in the same manner as in Example 3B except that the acrylic elastomer sheet having a thickness of 2 mm was changed to the following polyester-based elastomer (polyester-based thermoplastic elastomer) sheet.

A polyester-based elastomer sheet having a thickness of 2 mm was produced using "PRIT 30" produced by Bell Polyester Products, Inc., which was a block copolymer of a hard block and a soft block, as a resin pellet of a polyester-based elastomer.

The hard block was a structural unit derived from ester and the soft block was a structural unit derived from ester polyol, and the glass transition temperature (Tg) of the hard block was higher than the glass transition temperature (Tg) of the soft block, in PRIT 30.

Example 5B

A mouthpiece (layer (A)) made of a polyester-based elastomer was first obtained in the same manner as in Example 4B.

Next, Erkodul manufactured by ERKODENT (polyester sheet, 1 mm in thickness) was heat-sealed to the layer (A) by suction molding at a stage of being softened and hung by 1.5 cm, by use of the mandible model where the mouthpiece (layer (A)) was formed and the molding machine (Modelcapture Try). As described above, a layered mouthpiece (total thickness: 3 mm) was obtained. Erkodul was a sheet of glycol-modified polyethylene terephthalate (PETG).

Example 6B

A mouthpiece (layer (A)) made of an acrylic elastomer was first obtained in the same manner as in Example 1B.

Next, Erkodul manufactured by ERKODENT (polyester sheet, 0.5 mm in thickness) was heat-sealed to the layer (A) by suction molding at a stage of being softened and hung by 1.5 cm, by use of the mandible model where the mouthpiece (layer (A)) was formed and the molding machine (Modelcapture Try). As described above, a layered mouthpiece (total thickness: 2.5 mm) was obtained.

Examples 7B to 9B

Each layered mouthpiece was obtained in the same manner as in Example 6B except that the thickness of the polyester sheet (Erkodul) was changed.

Comparative Examples 1B to 3B

Each layered mouthpiece (total thickness: 3 mm) was obtained in the same manner as in each of Examples 1B, 2B and 5B except that the acrylic elastomer sheet was changed to Erkoflex manufactured by ERKODENT (ethylene-vinyl acetate copolymer sheet, 2 mm in thickness).

Comparative Example 4B

A layered mouthpiece (total thickness: 3 mm) was obtained in the same manner as in Comparative Example 3B except that a surface of the layer (A) (to which the layer (B) was to be heat-sealed) was coated with Super-Bond (produced by Sun Medical Co. Ltd.) as a dental adhesive, before the layer (B) was heat-sealed to the layer (A) by suction molding.

Comparative Example 5B

Erkocryl manufactured by ERKODENT (PMMA sheet: 2 mm in thickness) was subjected to suction molding at a stage of being softened and thus hung by 1.5 cm, by use of the mandible model and the molding machine (Modelcapture Try) used in Example 1B, thereby providing a monolayer mouthpiece made of PMMA (total thickness: 2 mm).

TABLE 3

| | | Example 1B | Example 2B | Example 3B | Example 4B | Example 5B | Example 6B | Example 7B | Example 8B | Example 9B |
|---|---|---|---|---|---|---|---|---|---|---|
| Layer (A) | | Acrylic elastomer | Acrylic elastomer (rough polishing) | Acrylic elastomer | Polyester-based elastomer | Polyester-based elastomer | Acrylic elastomer | Acrylic elastomer | Acrylic elastomer | Acrylic elastomer |
| Layer (B) | | PMMA (polymerization) | PMMA (polymerization) | PMMA (heat-sealing) | PMMA (heat-sealing) | Polyester (heat-sealing) | Polyester (heat-sealing) | Polyester (heat-sealing) | Polyester (heat-sealing) | Polyester (heat-sealing) |
| Thickness (mm) of layer (A) | | 2 | 2 | 2 | 2 | 2 | 2 | 2 | 2 | 2 |
| Thickness (mm) of layer (B) | | 1 | 1 | 1 | 1 | 1 | 0.5 | 1 | 2 | 3 |
| Total thickness (mm) | | 3 | 3 | 3 | 3 | 3 | 2.5 | 3 | 4 | 5 |
| Layer (A) | Bending elastic modulus ($\alpha$) (MPa) | 177 | 177 | 177 | 144 | 144 | 177 | 177 | 177 | 177 |
| | Shore A hardness | 75 | 75 | 75 | 95 | 95 | 75 | 75 | 75 | 75 |

TABLE 3-continued

|  |  | Example 1B | Example 2B | Example 3B | Example 4B | Example 5B | Example 6B | Example 7B | Example 8B | Example 9B |
|---|---|---|---|---|---|---|---|---|---|---|
|  | Water absorption rate (% by mass) | 0.59 | 0.59 | 0.59 | 0.38 | 0.38 | 0.59 | 0.59 | 0.59 | 0.59 |
| Layer (B) | Bending elastic modulus (β) (MPa) | 2275 | 2275 | 2078 | 2078 | 2625 | 2625 | 2625 | 2625 | 2625 |
| Difference (β − α) in elastic modulus between layer (A) and layer (B) (MPa) |  | 2098 | 2098 | 1901 | 1934 | 2481 | 2448 | 2448 | 2448 | 2448 |
| Adhesion strength between layer (A) and layer (B) (MPa) |  | >73 (*) | >130 (*) | >100 (*) | >100 (*) | >100 (*) | >100 (*) | >100 (*) | >100 (*) | >100 (*) |
| Wear feeling (Grade) |  | 3 | 3 | 3 | 3 | 3 | 3 | 3 | 3 | 3 |

TABLE 4

|  |  | Comparative Example 1B | Comparative Example 2B | Comparative Example 3B | Comparative Example 4B | Comparative Example 5B |
|---|---|---|---|---|---|---|
| Layer (A) |  | Ethylene/vinyl acetate copolymer | Ethylene/vinyl acetate copolymer (rough polishing) | Ethylene/vinyl acetate copolymer | Ethylene/vinyl acetate copolymer | PMMA |
| Layer (B) |  | PMMA (polymerization) | PMMA (polymerization) | Polyester (heat-sealing) | Polyester (adhesive and heat-sealing) |  |
| Thickness (mm) of layer (A) |  | 2 | 2 | 2 | 2 | 2 |
| Thickness (mm) of layer (B) |  | 1 | 1 | 1 | 1 |  |
| Total thickness (mm) |  | 3 | 3 | 3 | 3 | 2 |
| Layer (A) | Bending elastic modulus (α) (MPa) | 29 | 29 | 29 | 29 | 2078 |
|  | Shore A hardness | 86 | 86 | 86 | 86 | >99 |
|  | Water absorption rate (% by mass) | 0.14 | 0.14 | 0.14 | 0.14 | 1.45 |
| Layer (B) | Bending elastic modulus (β) (MPa) | 2275 | 2275 | 2625 | 2625 | 2078 |
| Difference (β − α) in sending elastic modulus between layer (A) and layer (B) (Mpa) |  | 2246 | 2246 | 2596 | 2596 | 0 |
| Adhesion strength between layer (A) and layer (B) (Mpa) |  | <5 | <5 | <5 | <5 | — |
| wear feeling (Grade) |  | 1 | 1 | 1 | 1 | 2 |

—Description of Table 3 and Table 4—

Symbol "(*)" in the column "Adhesion strength between layer (A) and layer (B) (MPa)" means the occurrence of material collapse of the layer (A) in breakage.

As represented in Table 3 and Table 4, the layered mouthpiece of each of Examples 1B to 9B was excellent in wear feeling (Grade 3). The layered mouthpiece of each of Examples 1B to 9B was also excellent in durability because of including the layer (B) high in bending elastic modulus.

On the other hand, the mouthpiece of each of Comparative Examples 1B to 4B, in which each ethylene-vinyl acetate copolymer was used as the material of the layer (A), did not almost obtain adhesion between the layer (A) and the layer (B) and was difficult to wear as a layered mouthpiece (Grade 1).

The monolayer mouthpiece made of PMMA, of Comparative Example 5B, caused any feeling of strangeness in wearing, and caused any pain on the row face of teeth in wearing (Grade 2).

Example 1C

An olefin-based polymer (A) was obtained as follows.

First, 250 mL of toluene was charged into a glass autoclave having an inner volume of 500 mL, sufficiently purged with nitrogen, and propylene was allowed to flow at a rate of 150 L/hour and kept at 25° C. for 20 minutes. A magnetic stirrer was placed in a side-arm flask having an inner volume of 30 mL, sufficiently purged with nitrogen, and 5.00 mmol of a solution of methylaluminoxane in toluene (Al=1.53 mol/L) and then 5.0 μmol of a solution of dibenzyl methylene(cyclopentadienyl)(3,6-di-tert-butylfluorenyl)zirconium dichloride in toluene were added thereto and stirred for 20 minutes. The resulting solution was added to the glass autoclave with toluene into which propylene was allowed to flow, and polymerization was initiated. Polymerization was performed under ordinary pressure at 25° C. for 45 minutes with a propylene gas being continuously fed at a rate of 150

L/hour, and thereafter a small amount of methanol was added to stop the polymerization. A polymer solution was added to an excess of methanol to precipitate a polymer, and the polymer was subjected to drying under reduced pressure at 80° C. for 12 hours, thereby consequently providing 2.38 g of a propylene polymer (syndiotactic olefin as an olefin-based polymer (A)). The polymerization activity was 0.63 kg-PP/mmol-Zr·hr, and the resulting propylene polymer had a limiting viscosity [η] of 1.9 dL/g, a melting point Tm of 158° C. (Tm1=152° C., Tm2=158° C.), a pentad ratio (rrrr ratio) of 93.5%, a melting heat quantity ($\Delta H_C$) of 57 J/g and a Mw/Mn of 2.0. The MFR (ASTM D 1238, 230° C., a load of 2.16 kg) was 6.0 g/10 min.

Next, an olefin-based monolayer sheet having a thickness of 2 mm was produced using the propylene polymer obtained as above. Next, an olefin-based mouthpiece was produced in the same manner as in Example 1A.

Example 2C

After 30% by mass of Exfola (registered trademark, produced by Mitsui Chemicals, Inc., olefin-based modification material) was kneaded with the propylene polymer obtained in the same manner as in Example 1C, an olefin-based monolayer sheet having a thickness of 2 mm was produced. Next, an objective olefin-based mouthpiece was obtained by the same operation as in Example 1C.

Comparative Examples 1C to 3C

Respective monolayer sheets having a thickness of 2 mm and respective mouthpieces were produced in the same manner as in Example 1C except that Erkoflex (manufactured by ERKODENT) which was an ethylene-vinyl acetate copolymer sheet, Erko-lock Pro (manufactured by ERKODENT) which was a thermoplastic polyurethane sheet and Erkodul (manufactured by ERKODENT) which was a PMMA sheet were used, respectively, and respective physical properties thereof were evaluated.

In Comparative Example 1C, the coffee staining property was high and the amount of sugar was also a large value. The polishing workability was also poor and the handleability was also inferior, while the sheet moldability was favorable.

In Comparative Example 2C, the Shore A hardness, the water absorption rate and the coffee staining property were high. The sheet moldability was also poor to unable to conduct mouthpiece formation, the polishing workability was also poor and the handleability was also inferior.

In Comparative Example 3C, the Shore A hardness and the bending elastic modulus were high, and the mouthpiece produced caused any pain when placed in the oral cavity. The water absorption rate and the coffee staining property were also high. Air bubbles were incorporated during sheet molding, the sheet moldability was not favorable, the polishing workability was also poor and the handling was also inferior.

TABLE 5

|  | Example 1C | Example 2C | Comparative Example 1C | Comparative Example 2C | Comparative Example 3C |
| --- | --- | --- | --- | --- | --- |
| Sheet material | Olefin | Olefin | Ethylene/vinyl acetate copolymer | Thermoplastic polyurethane | Polymethyl methacrylate |
| Thickness | 2 mm | 2 mm | 2 mm | 2 mm | 2 mm |
| Shore A hardness | 84 | 84 | 80 | 86 | >99 |
| Bending elastic modulus (Mpa) | 47 | 76 | 29 | 31 | 2050 |
| Impact resilience rate (%) | 6 | 16 | 15 | 15 | 32 |
| Water absorption rate (% by mass) | 0.03 | 0.03 | 0.14 | 3 | 1.45 |
| Coffee staining property (ΔE) | 0.29 | 0.45 | 9.1 | 47 | 2.17 |
| Amount of sugar (μg/mL) | 211 | — | 285 | — | — |
| Sheet moldability | 3 | 3 | 3 | 1 | 2 |
| Polishing workability | 5 | 5 | 3 | 1 | 2 |

The entireties of the disclosures of Japanese Patent Application No. 2016-044866 filed on Mar. 8, 2016, Japanese Patent Application No. 2016-081807 filed on Apr. 15, 2016 Japanese Patent Application No. 2016-104694 filed on May 25, 2016 and Japanese Patent Application No. 2016-131886 filed on Jul. 1, 2016 are herein incorporated by reference.

All the Documents, patent applications and technical standards described herein are herein incorporated by reference to the same extent as if each individual document, patent application and technical standard were specifically and individually indicated to be incorporated by reference.

The invention claimed is:

1. A mouthpiece comprising a constituent portion (X), the constituent portion (X) comprising an olefin-based polymer (A) having a repeating unit having 2 or 3 carbon atoms and the constituent portion (X) satisfying a bending elastic modulus ($\alpha$) at 23° C. of 80 MPa≤$\alpha$≤1000 MPa,
   wherein the constituent portion (X) has a layered structure comprising:
   a layer (LI) that satisfies a bending elastic modulus ($\alpha$1) at 23° C. of 5 MPa≤$\alpha$1≤100 MPa; and
   a layer (LO) that satisfies a bending elastic modulus ($\alpha$2) at 23° C. of 200 MPa≤$\alpha$2≤1500 MPa.

2. The mouthpiece according to claim 1, wherein the constituent portion (X) is a piece unit to be worn on a row of teeth.

3. The mouthpiece according to claim 1, wherein the layer (LI) is exposed at at least a part of an outermost surface of the constituent portion (X).

4. The mouthpiece according to claim 3, wherein the constituent portion (X) is a portion to contact teeth when the mouthpiece is worn on a row of teeth, and the layer (LI) is exposed at at least a part of a surface of the portion that is to contact the teeth.

5. The mouthpiece according to claim 1, wherein the mouthpiece is a mouthpiece for temporomandibular joint syndrome or a mouthpiece for sleep apnea syndrome.

6. The mouthpiece according to claim 1, wherein the olefin-based polymer (A) has a structural unit derived from a siloxane structure.

7. A mouthpiece comprising a constituent portion (X), the constituent portion (X) comprising an olefin-based polymer (A) having a repeating unit having 2 or 3 carbon atoms and the constituent portion (X) satisfying a Shore A hardness of more than 80 and less than 86, wherein the mouthpiece satisfies the following conditions (a) to (c):
(a) the olefin-based polymer (A) comprises, with respect to 100 parts by mass of the olefin-based polymer (A), from 51 parts by mass to 90 parts by mass of an olefin-based polymer component (A-1) having a melting point of from 100° C. to 170° C. measured according to a DSC method;
(b) the olefin-based polymer (A) comprises, with respect to 100 parts by mass of the olefin-based polymer (A), from 10 parts by mass to 49 parts by mass of an olefin-based polymer component (A-2) having a melting point of 95° C. or less or having substantially absent melting point, measured according to a DSC method; and
(c) the olefin-based polymer (A) has a bending elastic modulus ($\alpha$) at 23° C. of 5 MPa$\leq\alpha\leq$100 MPa.

* * * * *